(12) United States Patent
Glieberman et al.

(10) Patent No.: US 12,397,294 B2
(45) Date of Patent: Aug. 26, 2025

(54) MICROFLUIDIC TRAPPING CHIP AND USES THEREOF FOR CULTURE AND ASSAY OF CELL CLUSTERS AND OBJECTS

(71) Applicant: President and Fellows of Harvard College, Cambridge, MA (US)

(72) Inventors: Aaron L. Glieberman, Cambridge, MA (US); John P. Ferrier, Cambridge, MA (US); John F. Zimmerman, Boston, MA (US); Kevin Kit Parker, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 360 days.

(21) Appl. No.: 16/756,896

(22) PCT Filed: Oct. 19, 2018

(86) PCT No.: PCT/US2018/056701
§ 371 (c)(1),
(2) Date: Apr. 17, 2020

(87) PCT Pub. No.: WO2019/079714
PCT Pub. Date: Apr. 25, 2019

(65) Prior Publication Data
US 2021/0197196 A1    Jul. 1, 2021

Related U.S. Application Data

(60) Provisional application No. 62/620,148, filed on Jan. 22, 2018, provisional application No. 62/574,780, filed on Oct. 20, 2017.

(51) Int. Cl.
B01L 3/00        (2006.01)
C12M 3/06        (2006.01)
G01N 33/50       (2006.01)

(52) U.S. Cl.
CPC ... *B01L 3/502761* (2013.01); *B01L 3/502707* (2013.01); *C12M 23/16* (2013.01);
(Continued)

(58) Field of Classification Search
CPC ........ B01L 2200/0668; B01L 2200/12; B01L 2300/0883; B01L 3/502707;
(Continued)

(56) References Cited

U.S. PATENT DOCUMENTS

| 8,389,207 B2 | 3/2013 | Montminy et al. |
| 2004/0072278 A1* | 4/2004 | Chou ................. G01N 15/1456 436/63 |

(Continued)

FOREIGN PATENT DOCUMENTS

WO    2017/087759 A1    5/2017

OTHER PUBLICATIONS

Xu et al. Optimization of microfluidic microsphere-trap arrays. Biomicrofluidics. Feb. 27, 2013;7(1):14112. doi: 10.1063/1.4793713. PMID: 24404004; PMCID: PMC3598822. (Year: 2013).*

(Continued)

*Primary Examiner* — Jennifer Wecker
*Assistant Examiner* — Jonathan Bortoli
(74) *Attorney, Agent, or Firm* — McCarter & English, LLP; Maria Laccotripe Zacharakis; Anita M. Bowles

(57) ABSTRACT

Some embodiments provide a microfluidic cartridge for automatically hydrodynamically loading objects (e.g., cell clusters) into traps in parallel trapping channels with one object per trap, methods of making such cartridges and methods of use of such cartridges.

15 Claims, 22 Drawing Sheets

(52) U.S. Cl.
CPC .. *G01N 33/5008* (2013.01); *B01L 2200/0668* (2013.01); *B01L 2200/12* (2013.01); *B01L 2300/0883* (2013.01)

(58) Field of Classification Search
CPC ....... B01L 3/502761; B01L 2200/0621; B01L 2200/0642; B01L 2300/0864; B01L 2300/0867; B01L 2300/10; B01L 2400/086; B01L 3/502746; B01L 3/00; C12M 23/16; G01N 33/5008; G01N 15/10; G01N 15/12; G01N 15/14; G01N 15/1484; G01N 2015/1006; G01N 2800/042; G01N 33/48; G01N 33/483; G01N 33/487; G01N 33/50; G01N 33/507; G01N 33/53; G01N 33/543; G01N 33/554; G01N 30/91; G01N 35/02; H04B 7/0452; H04B 7/0632; H04B 7/0634; H04W 16/28; C12Q 1/686
See application file for complete search history.

(56) References Cited

U.S. PATENT DOCUMENTS

| | | | |
|---|---|---|---|
| 2007/0184494 A1 | 8/2007 | McBride et al. | |
| 2010/0252118 A1* | 10/2010 | Fraden | G01N 15/1484 137/825 |
| 2010/0273681 A1* | 10/2010 | Cerrina | B01L 3/502776 506/40 |
| 2011/0117634 A1* | 5/2011 | Halamish | C12M 23/16 435/283.1 |
| 2013/0078163 A1* | 3/2013 | Chung | C12M 21/06 422/502 |
| 2013/0190212 A1* | 7/2013 | Handique | G01N 15/1436 506/40 |
| 2013/0260474 A1* | 10/2013 | Chan | B01F 33/3039 422/68.1 |
| 2014/0151224 A1 | 6/2014 | Glezer et al. | |
| 2015/0087559 A1 | 3/2015 | Putnam et al. | |
| 2015/0343444 A1 | 12/2015 | Manalis et al. | |
| 2016/0339430 A1 | 11/2016 | White et al. | |
| 2016/0361716 A1 | 12/2016 | Solomon | |
| 2018/0327702 A1 | 11/2018 | Gannon et al. | |

OTHER PUBLICATIONS

Xiaoxiao Xu et al "Optimization of microfluidic microsphere-trap arrays", Biomicrofluidics 7, 014112 https://doi.org/10.1063/1.4793713 (Year: 2013).*

Deng, Bin et al. "Parameter Screening in Microfluidics Based Hydrodynamic Single-Cell Trapping." The Scientific World Journal (Year: 2014).*

Khalili et al. 2016. "A Microfluidic Device for Hydrodynamic Trapping and Manipulation Platform of a Single Biological Cell" Applied Sciences 6, No. 2: 40. https://doi.org/10.3390/app6020040 (Year: 2016).*

Yesilkoy et al , "Highly efficient and gentle trapping of single cells in large microfluidic arrays for time-lapse experiments", Biomicrofluidics 10, 014120 https://doi.org/10.1063/1.4942457 (Year: (201) (Year: 2016).*

Glieberman et al "Synchronized stimulation and continuous insulin sensing in a microfluidic human Islet on a Chip designed for scalable manufacturing" DOI: 10.1039/C9LC00253G (Paper) Lab Chip, 19, 2993-3010 (Year: 2019).*

Kim et al ("A high-efficiency microfluidic device for size-selective trapping and sorting") Lab Chip; 14(14): 2480-2490. doi:10.1039/c4lc00219a (Year: 2014).*

Zhou et al "A microfluidic platform for trapping, releasing and super-resolution imaging of single cells", Sensors and Actuators B: Chemical, vol. 232, 2016, pp. 680-691, ISSN 0925-4005, (Year: 2016).*

Saralidze ("Polymeric Microspheres for Medical Applications") Materials 2010, 3, 3537-3564; doi:10.3390/ma3063537 (Year: 2010).*

Nguyen ("Hydrodynamic trapping for rapid assembly and in situ electrical characterization of droplet interface bilayer arrays") Lab Chip, 2016, 16, 357. (Year: 2016).*

International Search Report and Written Opinion for Application No. PCT/US2018/056701, dated Jan. 4, 2019, 10 pages.

* cited by examiner

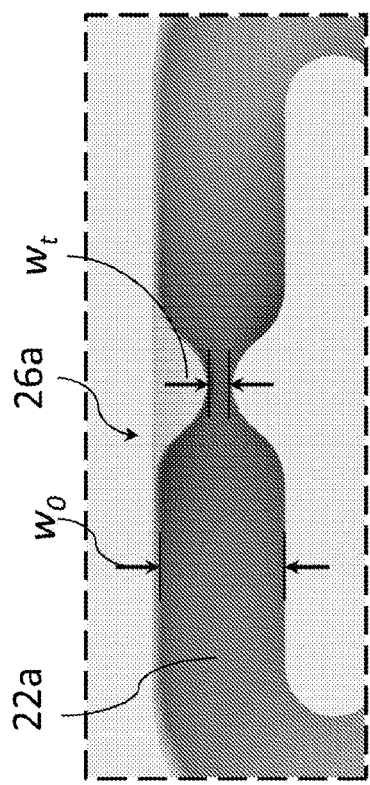
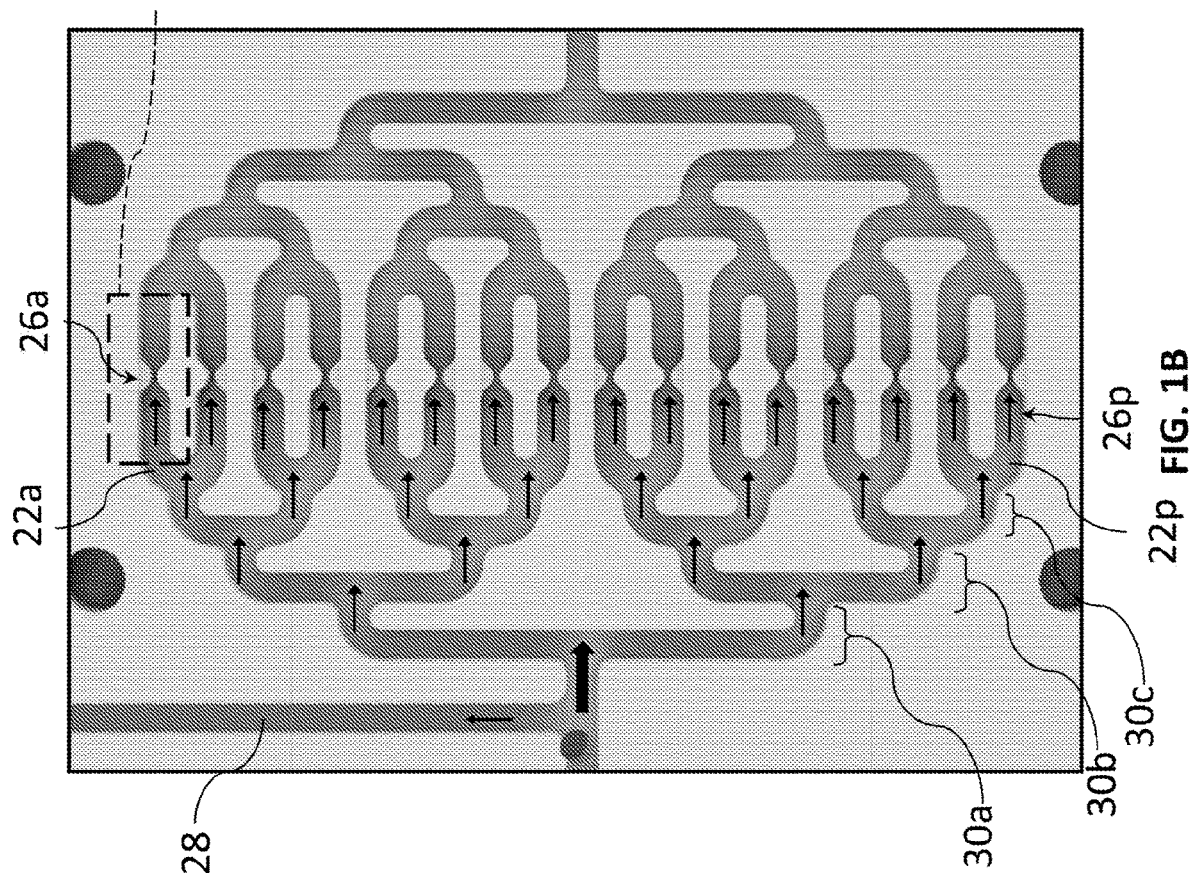
FIG. 1C
FIG. 1B

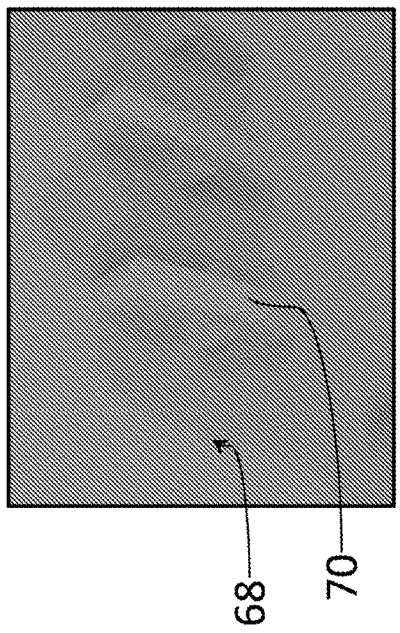
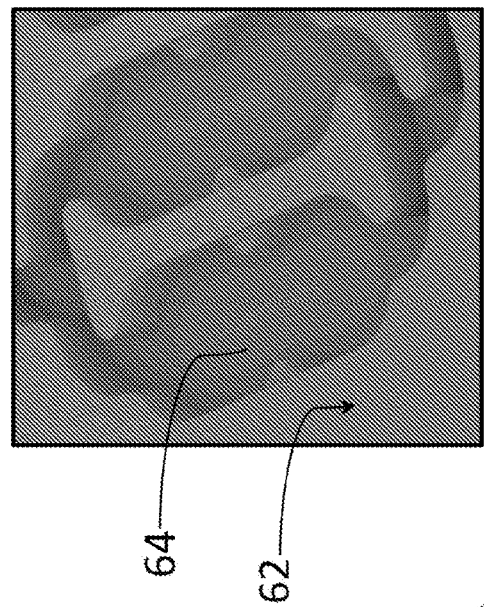
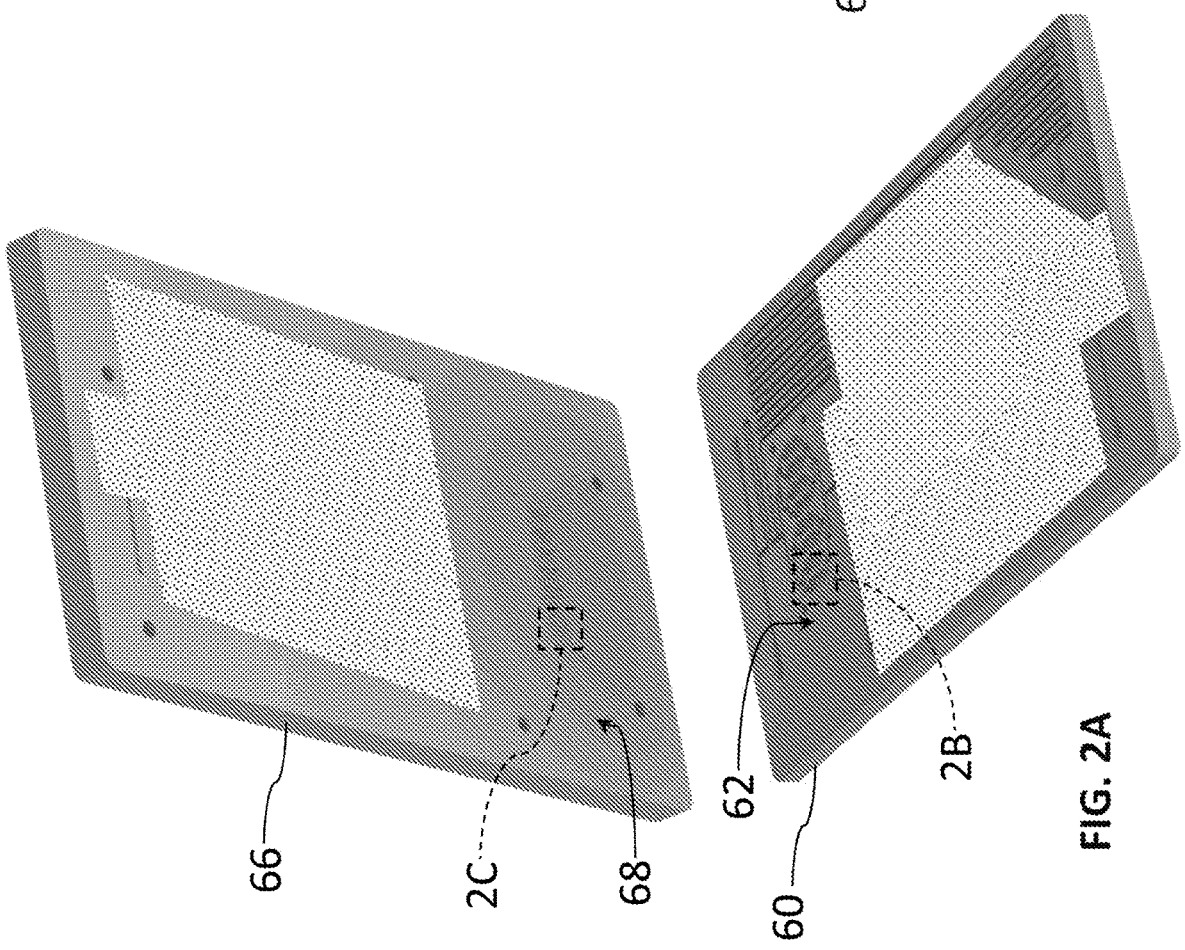
FIG. 2C
FIG. 2B
FIG. 2A

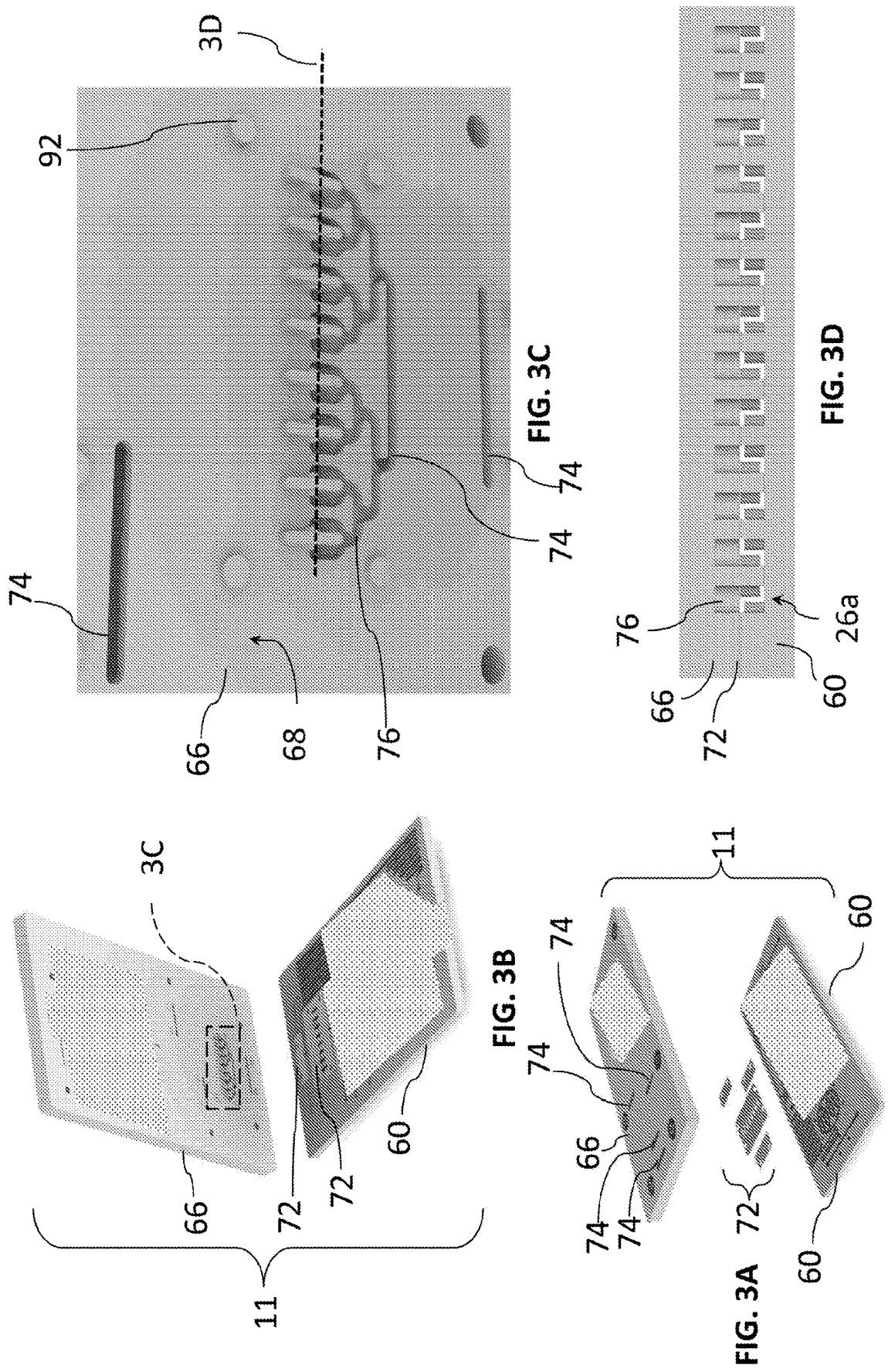

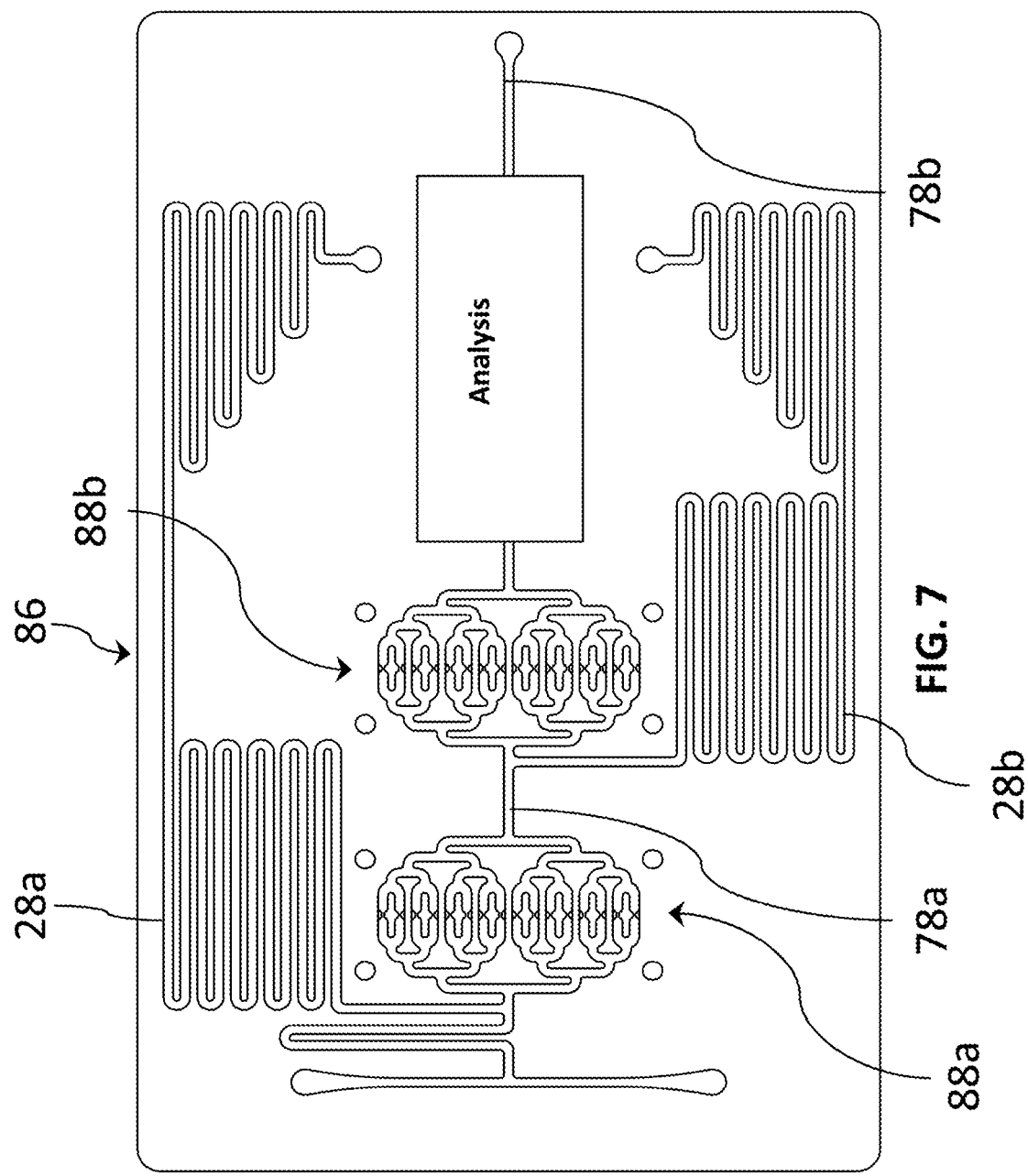

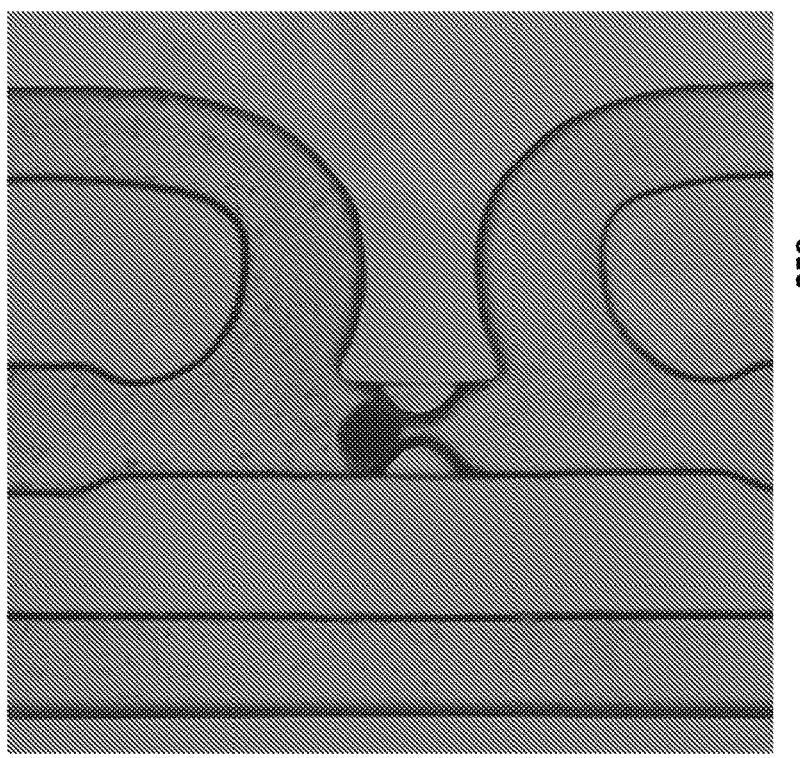
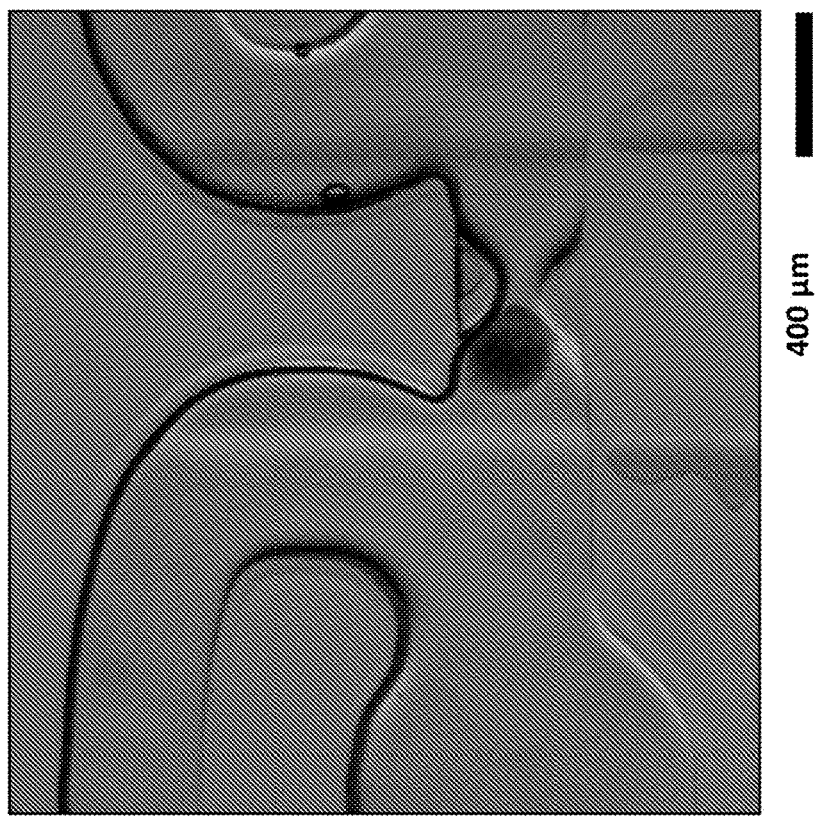
FIG. 13

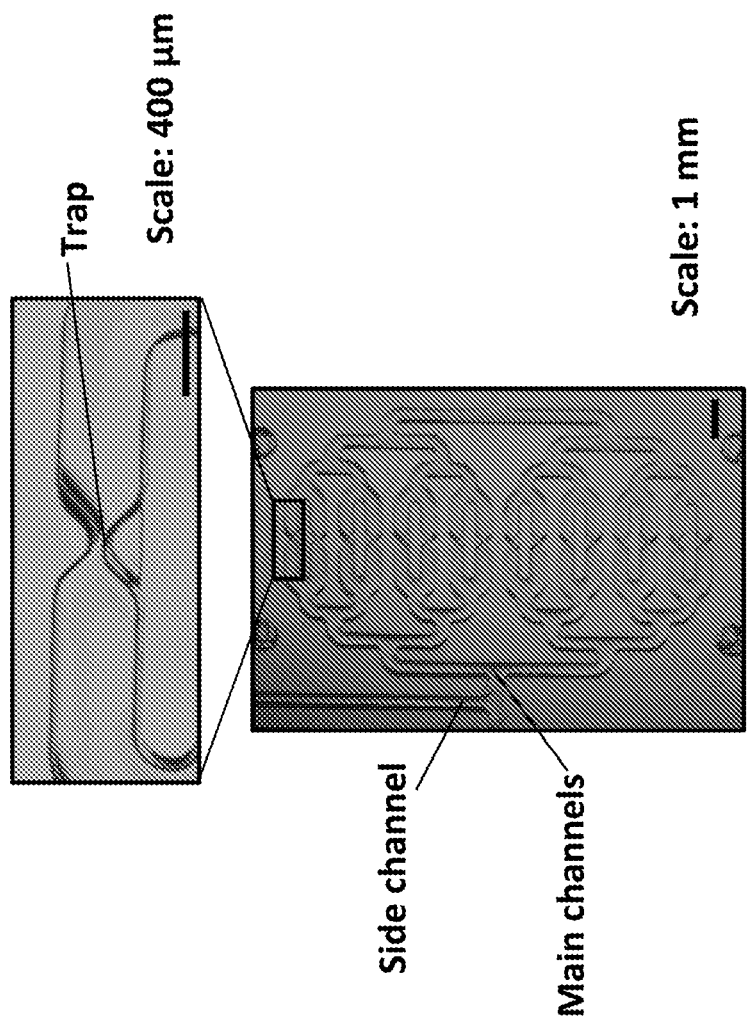
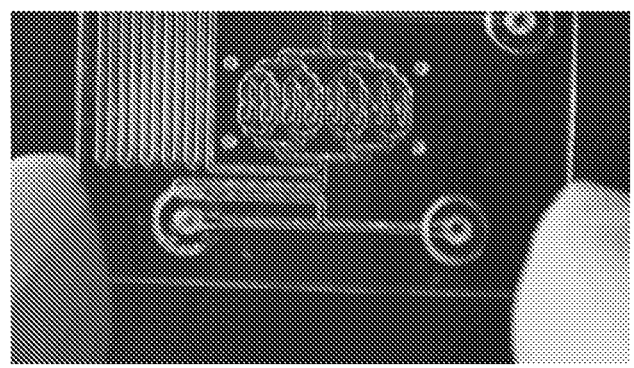
FIG. 15

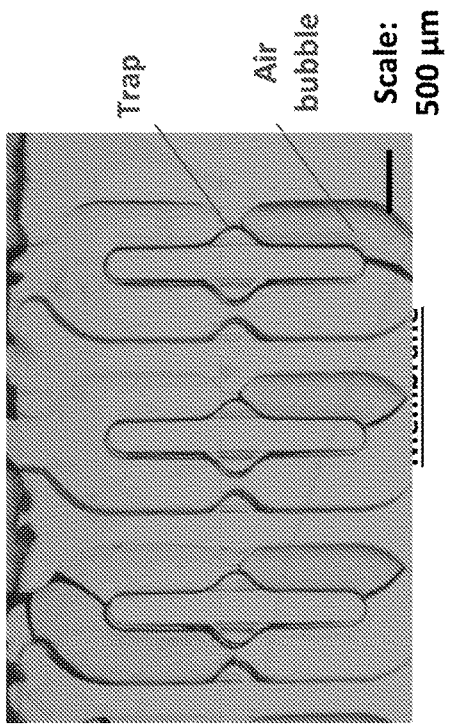
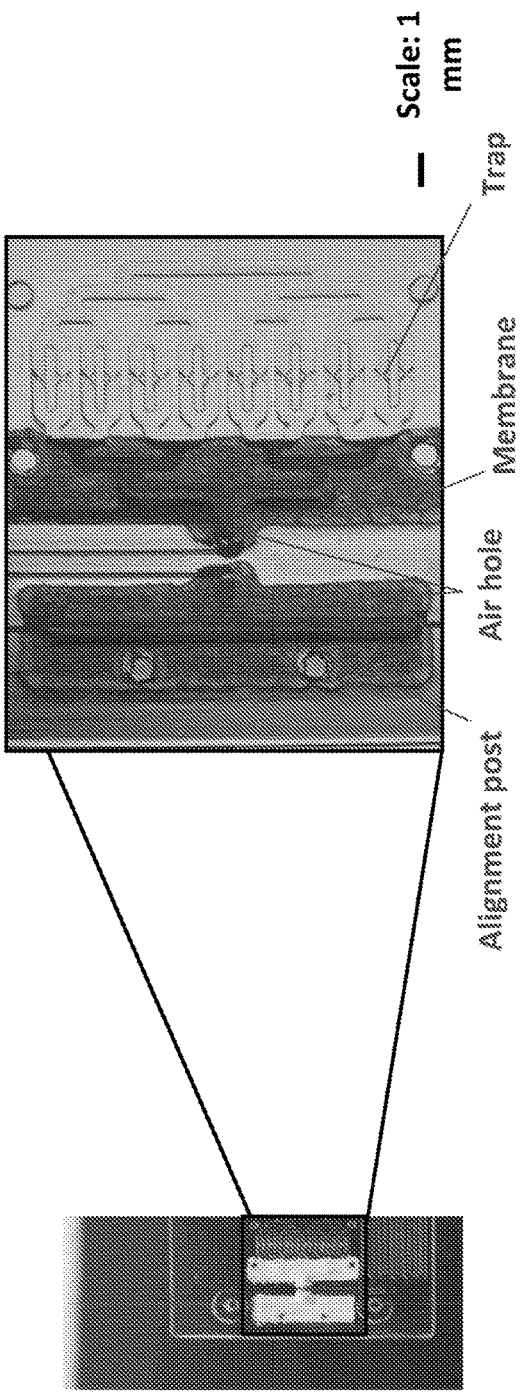
FIG. 17

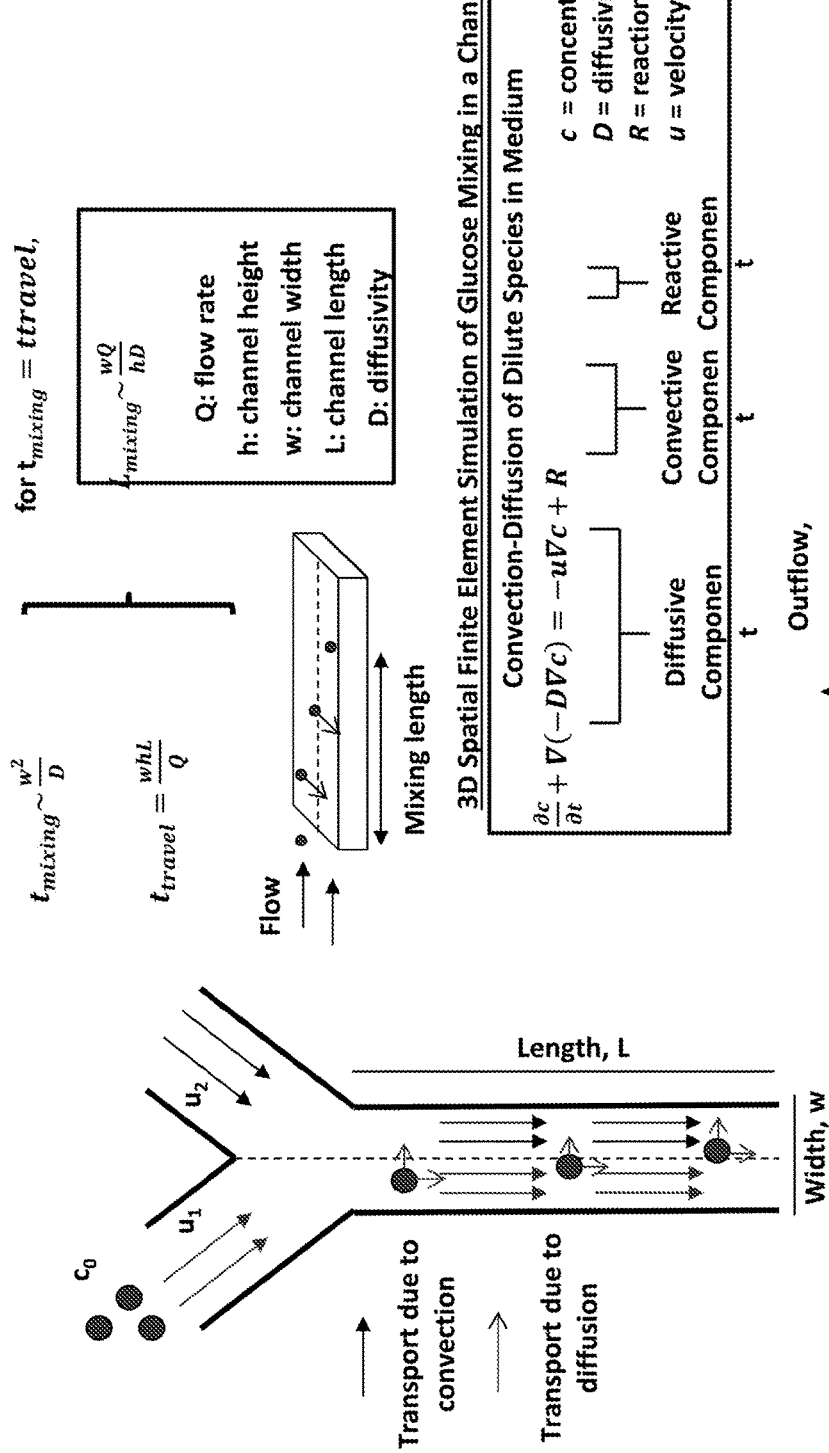
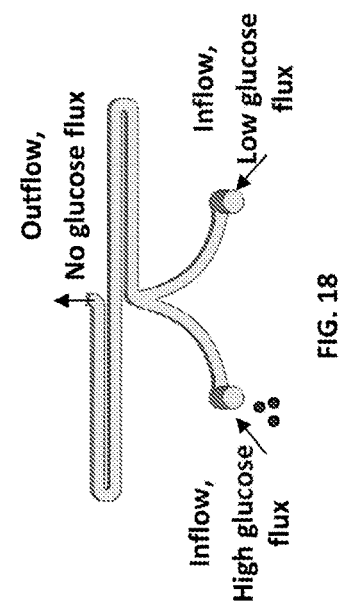
FIG. 18

MICROFLUIDIC TRAPPING CHIP AND USES THEREOF FOR CULTURE AND ASSAY OF CELL CLUSTERS AND OBJECTS

RELATED APPLICATIONS

This application is a 35 U.S.C. § 371 national stage filing of International Application No. PCT/US2018/056701, filed on Oct. 19, 2018, which claims the benefit of priority to U.S. Provisional Application No. 62/574,780, filed on Oct. 20, 2017, and U.S. Provisional Application No. 62/620,148, filed on Jan. 22, 2018. The entire contents of each of the aforementioned applications are incorporated herein by reference.

GOVERNMENT SUPPORT

This invention was made with government support under DK104165, and ES027272 awarded by the National Institutes of Health, and W911NF-12-2-0036 awarded by the Army Research Laboratory—Army Research Office. The government has certain rights in the invention.

BACKGROUND OF THE INVENTION

When conducting experiments with organoids or cell clusters, conventional cell culturing methods have employed a well-based platform where a suspension of clusters is manually introduced to a reservoir of a defined size containing medium. For culturing a specific number of clusters, the clusters are counted one by one—often under a microscope—before addition to the well. Clusters in such a well-based platform are not spaced evenly from one another, meaning that they will each experience differences in the oxygenation, nutrient content, and feedback mechanisms based on the number and proximity of their neighbors. Additionally, because the clusters rest in a static volume of culture medium, the cells of the clusters have a finite amount of nutrients that can be depleted while waste is accumulating around the cells. Microfluidic devices as applied to cell culture have emerged in the past few decades to address the issues of oxygenation, nutrient delivery, and waste removal to produce a culture environment more akin to perfused tissue in vivo; however, conventional microfluidic devices for culturing cell clusters are still hindered by similar issues relating to cell seeding and placement. Like well-based culture systems, it is often difficult to load cell clusters in conventional microfluidic devices in a consistent and uniform fashion. Further, many conventional microfluidic devices for culturing cell clusters arrange the cells clusters in series such that a flow that has interacted with one cluster subsequently interacts with another cluster downstream subjecting the downstream cluster to influence from interaction between the fluid flow and the upstream cluster.

Materials issues have also limited the wide scale adoption of some conventional microfluidic platforms. Many conventional microfluidic devices are made of polydimethylsiloxane (PDMS), an elastomer that has facilitated research in microfluidic systems at an academic level but has not shown great promise as a material for fabricating devices at a commercial scale. Additionally, devices composed of PDMS are prone to shape change as a result of water absorption, which can impact the performance and reliability of such devices. Furthermore, PDMS has a tendency to absorb and retain materials from the culture medium. These materials considerations, combined with the greater issues of the difficulties in loading and cell-cell influence, hinder the ability for conventional microfluidic devices to provide a scalable and reliable method for culturing cell clusters.

Accordingly, there is a need for improved microfluidic devices for loading and culturing of cell clusters and organoids.

SUMMARY OF THE INVENTION

In one aspect, the present invention provides a microfluidic chip for trapping a plurality of objects. The microfluidic chip includes a body including: one or more inlets; one or more outlets; a plurality of trapping channels in parallel with each other, the plurality of trapping channels connected with at least one of the one or more inlets in an upstream direction and with at least one of the one or more outlets in a downstream direction, each trapping channel including a hydrodynamic trap configured to trap an object having a diameter in a specified sub-millimeter range; and a bypass channel arranged in parallel with and associated with at least one of the plurality of trapping channels, an upstream end of the bypass channel is connected with at least one of the one or more inlets and a downstream end of the bypass channel connected with at least one of the one or more outlets, the bypass channel and the associated at least one of the plurality of trapping channels being configured such that an object in a fluid introduced through the one or more inputs that flows into a channel directly upstream of the bypass channel preferentially flows into an empty trap of the associated at least one of the plurality of trapping channels when there is an empty trap in the associated at least one of the plurality of trapping channels, and such that the object preferentially flows into the bypass channel when none of the associated at least one of the plurality of trapping channels has an empty trap.

In some embodiments, the bypass channel is associated with every trapping channel in the plurality of trapping channels and wherein the bypass channel branches from a channel upstream of all of the plurality of trapping channels.

In some embodiments, the at least one output includes a bypass output that receives output from the bypass channel and one or more trap outputs that receive output from the plurality of trapping channels but do not receive output from the bypass channel.

In some embodiments, the bypass output is configured to be blocked to reduce or stop flow into the bypass channel after completion of loading of the microfluidic chip with objects.

In some embodiments, the body includes a plurality of bypass channels in parallel with each other, each bypass channel being associated with one of the plurality of trapping channels, each bypass channel and the associated trapping channel being configured such that an object in a fluid flowing in a channel directly upstream of the bypass channel preferentially flows into the trap of the associated trapping channel when the trap is empty, and preferentially flows into the bypass channel when the trap of the associated trapping channel already has a trapped object.

In some embodiments, a flow resistance along a flow path from one of the one or more inputs through the trap and to one of the one or more outputs is the same for each of the plurality of trapping channels when the traps of the plurality of trapping channels are empty.

In some embodiments, a flow path distance from one of the one or more inputs to the trap is the same for each of the plurality of trapping channels.

In some embodiments, a flow path distance a trap to the one or more output is the same for each of the plurality of trapping channels.

In some embodiments, for each of the trapping channels, a width of the trapping channel at the trap narrows over at least a portion of a height of the trapping channel.

In some embodiments, the at least one inlet includes at least two inlets, and wherein the microfluidic chip includes a mixing channel that connects with the at least two inlets and connects with an upstream side of the plurality of trapping channels.

In some embodiments, the mixing channel is configured to mix input fluid from the at least two inlets.

In some embodiments, a first trapping channel of the plurality of trapping channels has a first trap and includes a base surface, a top surface opposite the base surface, a first sidewall, and a second sidewall opposite the first sidewall, the first trapping channel having a first height at the first trap, and wherein the first trap of the first trapping channel includes: a first protrusion extending from the first sidewall toward the second sidewall and extending from the base surface toward the top surface of the first channel, with the first protrusion having a height less than first height forming a first shelf with a first top gap separating the first shelf from the top surface of the first trapping channel: a second protrusion extending from the second sidewall toward the first sidewall and extending from the top surface toward the base surface of the first channel, with the second protrusion having a height less than the first height forming a first overhang with a first bottom gap separating first overhang from the base surface of the first trapping channel, the second protrusion disposed opposite the first protrusion such that a first lateral gap separates the first protrusion and the second protrusion over a portion of the first height.

In some embodiments, a narrowing of the first trapping channel at the first lateral gap is configured to trap an object, and wherein the first top gap and the first bottom gap enable fluid to flow around the trapped object while being small enough to prevent the object from passing through the first top gap and the first bottom gap.

In some embodiments, a second trapping channel in the plurality of trapping channels has a second trap and includes a base surface, a top surface opposite the base surface, a third sidewall, and fourth sidewall opposite the third sidewall, the second trapping channel having a second height at the second trap, and wherein the second trap of the second trapping channel includes: a third protrusion extending from the third sidewall toward the fourth sidewall and extending from the base surface toward the top surface of the second channel, with the third protrusion having a height less than the second height forming a second shelf with a second top gap separating second shelf from the top surface of the second trapping channel: a fourth protrusion extending from the fourth sidewall toward the third sidewall and extending from the top surface toward the base surface of the second trapping channel, with the fourth protrusion having a height less than the second height forming a second overhang with a second bottom gap separating the second overhang from the bottom surface of the second trapping channel, the third protrusion disposed opposite the fourth protrusion such that a second lateral gap separates the third protrusion and the fourth protrusion over a portion of the second height.

In some embodiments, a narrowing of the second trapping channel at the second lateral gap is configured to trap an object, and wherein the second top gap and the second bottom gap enable fluids to flow around the trapped object while being small enough to prevent the object from passing through the second top gap and the second bottom gap.

In some embodiments, the body comprises: a first portion; and a second portion that is attached to, coupled to, or fused with the first portion; wherein the first sidewall, first protrusion, third sidewall, and third protrusion, are formed by one or more recesses in a first surface of first portion that faces the second portion; and wherein the second sidewall, second protrusion, fourth sidewall, and fourth protrusion are formed by one or more projections from a second surface of the second portion that faces the first surface of the first portion.

In some embodiments, a shape of the one or more recesses in the first surface of the first portion is consistent with forming by machining, injection molding, or embossing of a single piece.

In some embodiments, a shape of the one or more protrusions from the second surface of the second portion is consistent with forming by machining, injection molding, or embossing of a single piece.

In some embodiments, the body comprises: a first portion including a first surface having one or more recesses; and a second portion attached to, coupled to, or fused with the first portion, a second surface of the second portion having one or more projections, the one or more recesses of the first portion and the one or more projections of the second portion cooperating to define the traps of the plurality of trapping channels, wherein each trap includes a first protrusion of a first sidewall of the trapping channel where first sidewall and the first protrusion are formed by the one or more recesses of the first portion, and a second protrusion of a second sidewall opposite the first protrusion formed by the one or more projections of the first portion, the first protrusion and the second protrusion separated by a lateral gap over at least a portion of a height of the trapping channel at the trap.

In some embodiments, the first protrusion of the first portion forms a ledge separated from a top surface of trapping channel formed by the second portion by a top gap; and wherein the second protrusion of the second portion forms an overhang separated by from a bottom surface of the trapping channel formed by the first portion by a bottom gap.

In some embodiments, the microfluidic chip further comprises one or more hydrophobic membranes disposed between the first portion and the second portion, the one or more membranes overlying one or more of: at least a portion of a recess in the first portion corresponding to an inlet channel connected to at least one of the one or more inlets; at least a portion of a recess in the first portion corresponding to a mixing channel downstream of the inlet channel and upstream of the plurality of trapping channels; and at least a portion of a recess in the first portion corresponding to the plurality of trapping channels; the second portion of the body including one or more holes, each extending through the second surface of the section portion where one of the one or more hydrophobic membranes overlies a recess corresponding to a channel of the microfluidic chip.

In some embodiments, at least one of the one or more holes enables gas that passes from the channel underlying the hydrophobic membrane and through the hydrophobic membrane to exit the microfluidic chip. In other embodiments, at least one of the one or more holes is configured to be connected to a source of gas for delivery for delivery of a gas or a component of the gas through the hydrophobic membrane and into the channel underlying the hydrophobic membrane.

In some embodiments, the second surface of the second portion comprises a groove that overlays at least a portion of a recess in the first portion that forms the channel underlying the hydrophobic membrane, the groove and the hydrophobic membrane forming a gas channel for the flow of gas between the at least one hole and the hydrophobic membrane.

In some embodiments, the microfluidic chips of the invention further comprise a second plurality of trapping channels in parallel with each other, each of the second plurality of trapping channels downstream of one or more of the first plurality of trapping channels, the second plurality of trapping channels each including a hydrodynamic trap configured to trap an object having a diameter in a diameter range smaller than a minimum trapping diameter for the traps of the first plurality of trapping channels.

In some embodiments, the body comprises a thermoplastic material.

In some embodiments, the object comprises one or more cells, e.g., one or more of a cell cluster, a hypertrophic adipocyte, an organoid, cells encapsulated in a hydrogel.

In some embodiments, the object comprises a microbead or a microsphere.

In some embodiments, the microfluidic chip is configured for culturing the one or more cells of the trapped object.

In one aspect, the present invention provides a method of making the microfluidic chip of the invention. The methods includes forming the first portion with the first surface having the one or more recesses; forming the second portion with the second surface having one or more projections; attaching, coupling or fusing at least a portion of the first surface of the first portion to at least a portion of the second surface of the second portion, where the one or more recesses of the first portion and the one or more projections of the second portion cooperating to define the traps of the plurality of trapping channels.

In some embodiments, the method further comprises, prior to attaching, coupling or fusing at least a portion of the first surface of the first portion to at least a portion of the second surface of the second portion, disposing one or more hydrophobic membranes overlying one or more of: at least a portion of a recess in the first portion corresponding to an inlet channel connected to at least one of the one or more inlets and upstream of the bypass channel; at least a portion of a recess in the first portion corresponding to a mixing channel downstream of the inlet channel and upstream of the plurality of trapping channels; and at least a portion of a recess in the first portion corresponding to the plurality of trapping channels; wherein the formed second portion of the body includes one or more gas outlet holes, each extending through the second surface of the section portion where one of the one or more hydrophobic membranes overlies a recess corresponding to a channel of the microfluidic chip.

In some embodiments, the second surface of the second portion also has a groove that overlays at least a portion of a recess in the first portion that forms the channel underlying the hydrophobic membrane, the groove and the hydrophobic membrane forming a gas channel for the flow of gas between the at least one hole and the hydrophobic membrane in the resulting microfluidic chip.

In some embodiments, the first portion is formed, at least in part, by injection molding a material including a thermoplastic.

In some embodiments, the second portion is formed, at least in part, by injection molding.

In other embodiments, the first portion is formed, at least in part, by machining a polymeric material or hot embossing a polymeric material.

In other embodiments, the second portion is formed, at least in part, by machining a polymeric material or hot embossing a polymeric material.

In one aspect, the present invention provides a method of loading and culturing of cells. The method includes providing the microfluidic chip of the invention; delivering fluid including objects each comprising one or more cells into one of the one or more inlets of the microfluidic chip and hydrodynamically trapping an object comprising one or more cells in each trap; and delivering a cell culture medium to the microfluidic chip to culture the one or more cells of each object in the traps.

In some embodiments, the method further comprises blocking an outlet of the bypass channel after hydrodynamically trapping the objects.

In another aspect, the present invention provides a method for identifying a compound that modulates cell differentiation, cell viability, and/or cell function. The method includes providing the microfluidic chip of the invention; delivering fluid including objects each comprising one or more cells into one of the one or more inlets of the microfluidic chip and hydrodynamically trapping an object comprising one or more cells in each trap; contacting the trapped objects with a test compound; and determining the effect of the test compound on cell differentiation, cell viability, and/or cell function in the presence and absence of the test compound, wherein a modulation of cell differentiation, cell viability, and/or cell function in the presence of said test compound as compared to cell differentiation, cell viability, and/or cell function in the absence of said test compound indicates that said test compound modulates cell differentiation, cell viability, and/or function, thereby identifying a compound that modulates cell differentiation, cell viability, and/or function.

In yet another aspect, the present invention provides a method for identifying a compound useful for treating a disease or disorder. The method includes providing the microfluidic chip of the invention; delivering fluid including objects each comprising one or more cells into one of the one or more inlets of the microfluidic chip and hydrodynamically trapping an object comprising one or more cells in each trap; contacting the trapped objects with a test compound; and determining the effect of the test compound on cell differentiation, cell viability, and/or cell function in the presence and absence of the test compound, wherein a modulation of cell differentiation, cell viability, and/or cell function in the presence of said test compound as compared to cell differentiation, cell viability, and/or cell function in the absence of said test compound indicates that said test compound modulates cell differentiation, cell viability, and/or function, thereby identifying a compound useful for treating the disease or disorder.

In some embodiments, the objects comprise pancreatic islet cells and the effect of the test compound on pancreatic islet cell viability and/or function in the presence and absence of the test compound is determined.

In some embodiments, the disease or disorder is diabetes, the objects comprise pancreatic islet cells and the effect of the test compound on pancreatic islet cell viability and/or function in the presence and absence of the test compound is determined.

In another aspect, the present invention provides a method for identifying a compound useful for treating diabetes. The method includes providing the microfluidic chip of the invention; delivering fluid including objects comprising pancreatic islet cells into one of the one or more inlets of the microfluidic chip and hydrodynamically trapping an object comprising pancreatic islet cells in each trap; contacting the trapped object with a test compound; and determining the effect of the test compound on pancreatic islet cell viability and/or function in the presence and absence of the test compound, wherein a modulation of pancreatic islet cell viability and/or function in the presence of said test compound as compared to pancreatic islet cell viability and/or function in the absence of said test compound indicates that said test compound modulates pancreatic islet cell viability and/or function, thereby identifying a compound useful for treating diabetes.

BRIEF DESCRIPTIONS OF THE DRAWINGS

The features and advantages of the present disclosure will be more fully understood from the following description of exemplary embodiments when read together with the accompanying drawings. The drawings are intended to illustrate the teachings taught herein and are not intended to show relative sizes and dimensions unless otherwise noted, or to limit the scope of examples or embodiments. In the drawings, the same numbers are used throughout the drawings to reference like features and components of like function.

Figure 1A:
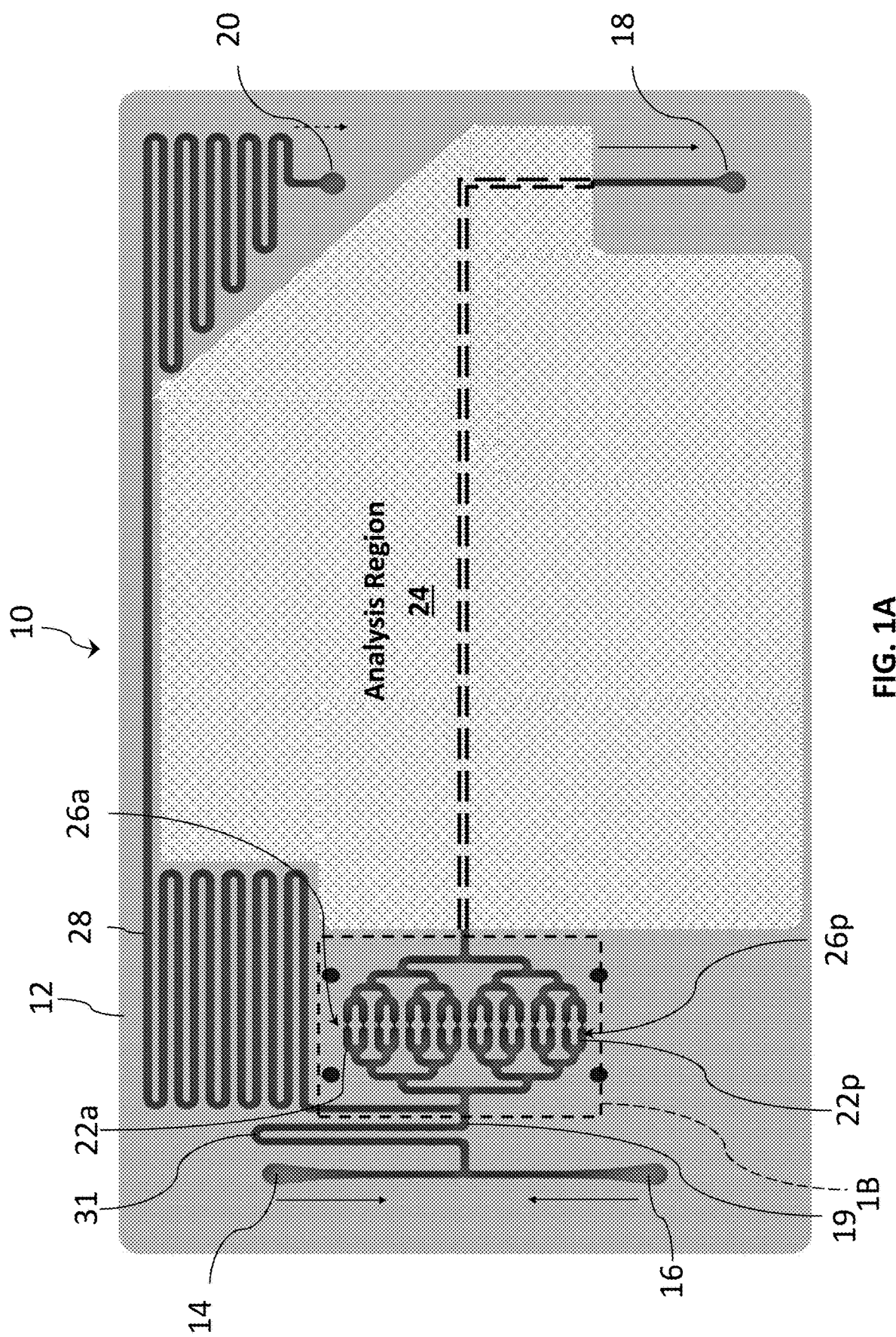
FIG. 1A is a plan view of a microfluidic chip including a plurality of trapping channels in parallel and a single bypass channel in accordance with some embodiments.
Figures 1D, 1E:
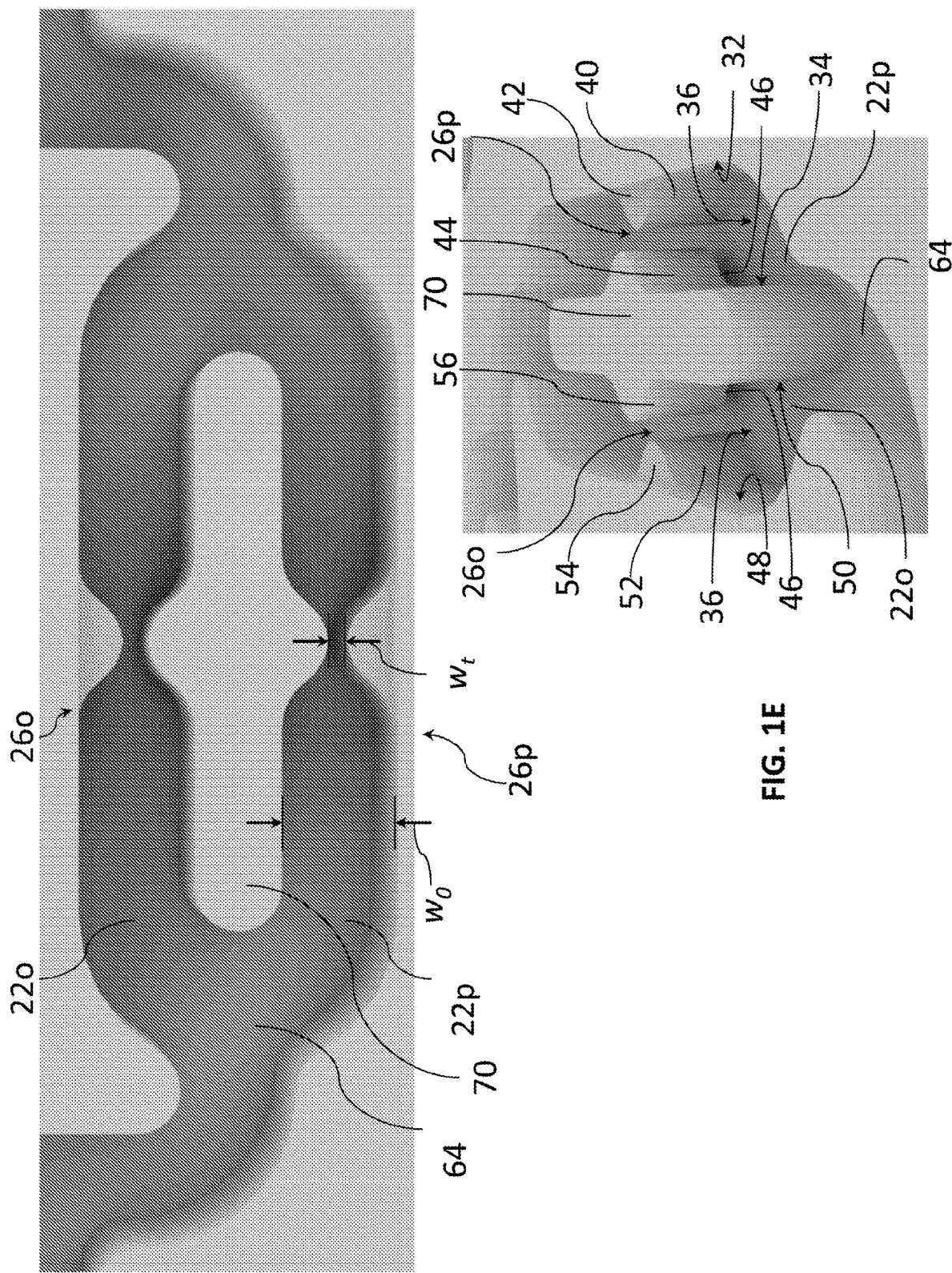
FIG. 1D is a detail of the trapping region of FIG. 1B showing a pair of traps.
FIG. 1E is a perspective view of the pair of traps shown in FIG. 1D.
Figure 1F:
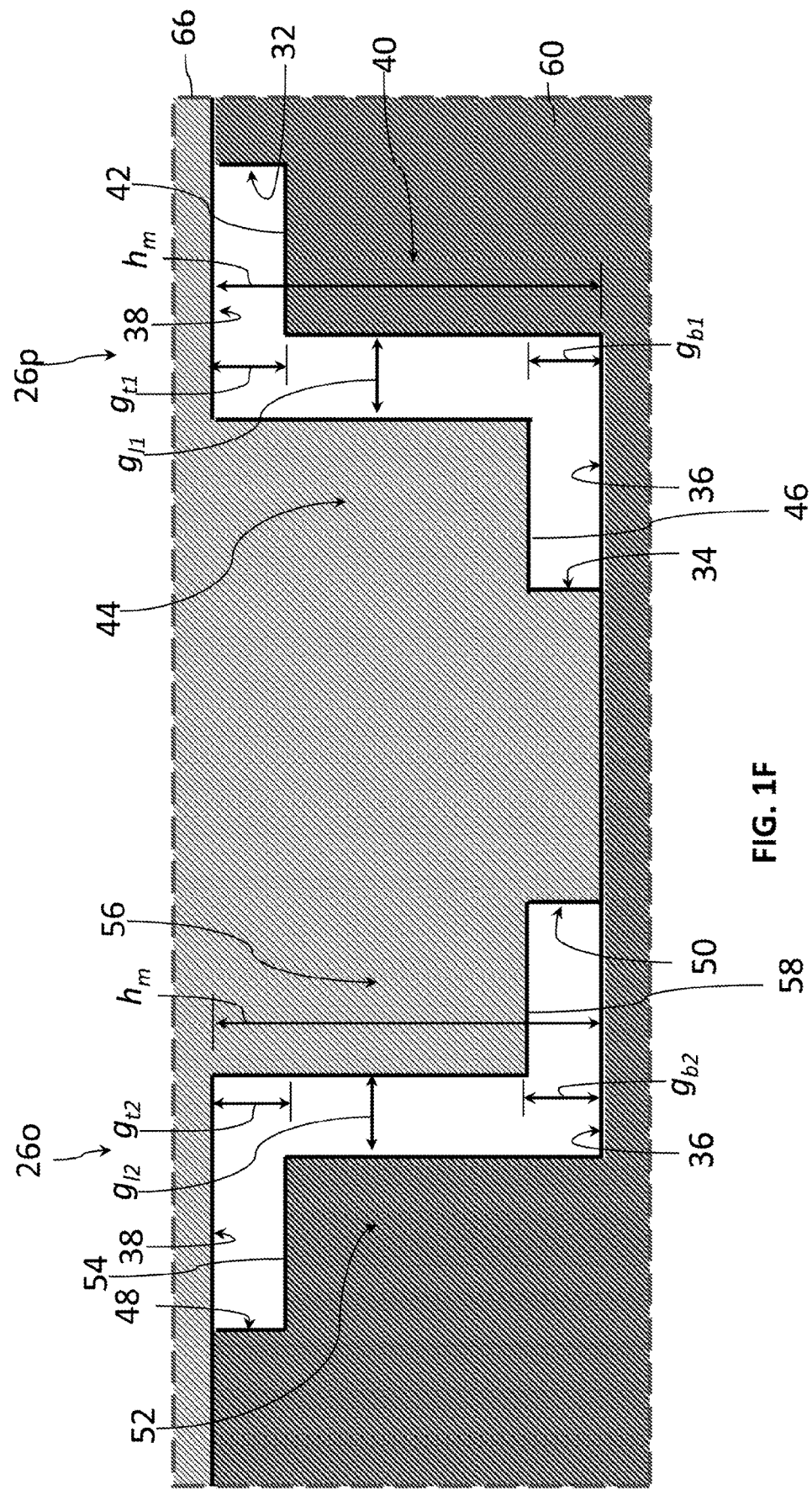
FIG. 1B is a detail of the microfluidic chip of FIG. 1A showing a trapping region.
FIG. 1C is a detail of the trapping region of FIG. 1B showing a single trap.

FIG. 1F schematically depicts is a cross sectional view of the pair of traps of FIG. 1D in accordance with some embodiment.

FIG. 2A is an exploded perspective view of a first portion and of a second portion of the microfluidic chip of FIG. 1A in accordance with some embodiments.

FIG. 2B is a detail of FIG. 2A showing a recess in a first surface of the first portion that forms a portion the pair of traps depicted in FIGS. 1E and 1F in accordance with some embodiments.

FIG. 2C is a detail of FIG. 2A showing a projection in a second surface of the second portion that cooperates with the recess in FIG. 2B to form the pair of traps depicted in FIGS. 1E and 1F in accordance with some embodiments.

FIG. 3A is an exploded view of a microfluidic chip incorporating hydrophobic membranes for gas exchange in accordance with some embodiments.

FIG. 3B is a partially exploded perspective view of the microfluidic chip of FIG. 3A with the hydrophobic membranes disposed on the first surface of the first portion.

FIG. 3C is a detail view of FIG. 3B showing holes through the second portion that connect with grooves in the second surface of the second portion that, along with the hydrophobic membranes, forming gas channels connecting with the holes in accordance with some embodiments.

FIG. 3D is a view of a cross section through line 3D in FIG. 3C showing the membrane, traps, and gas channels in accordance with some embodiments.

Figure 4A:
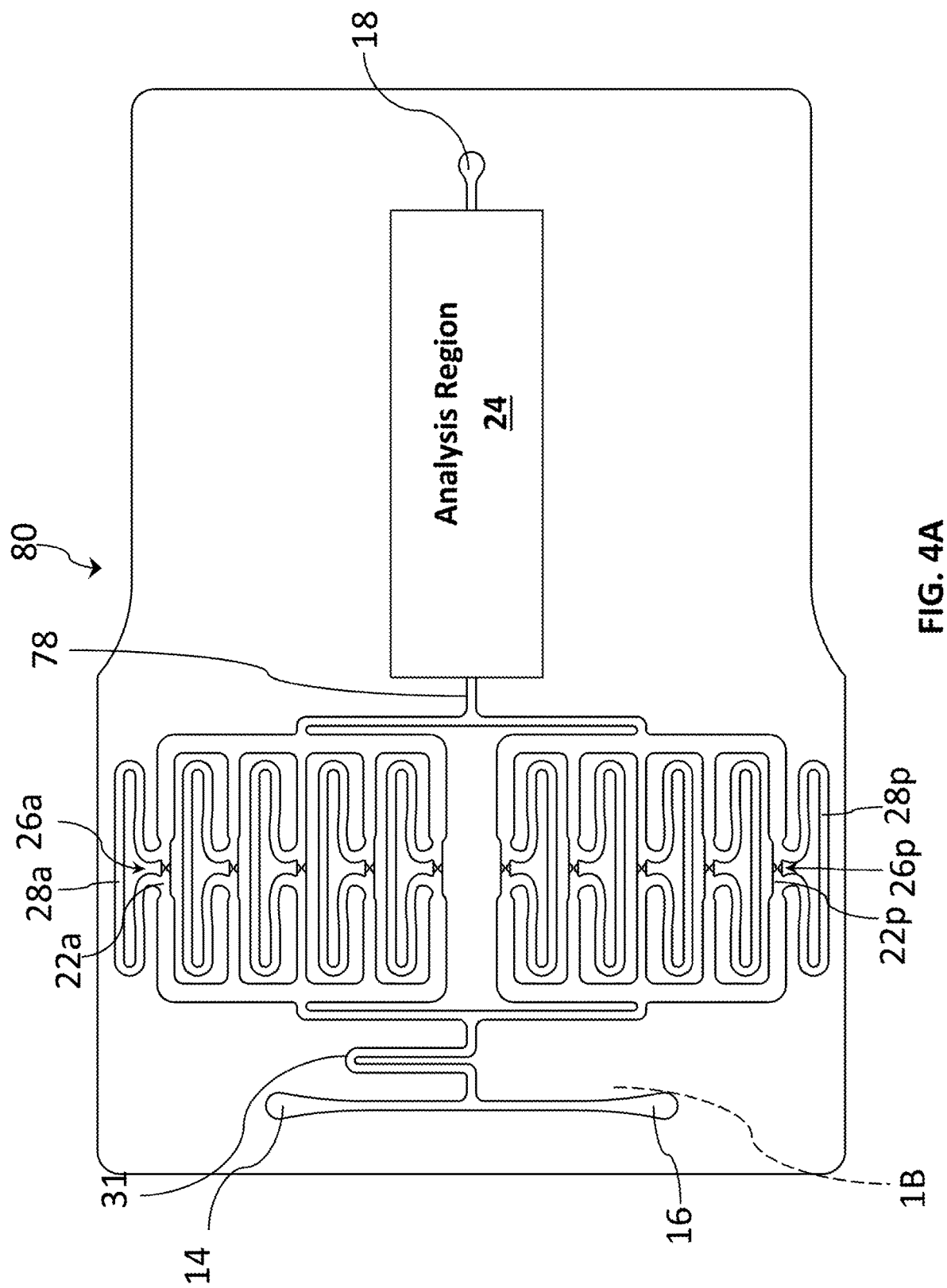

FIG. 4A is a plan view of a microfluidic chip including a bypass channel associated with each trapping channel in accordance with some embodiments.

Figure 4C:
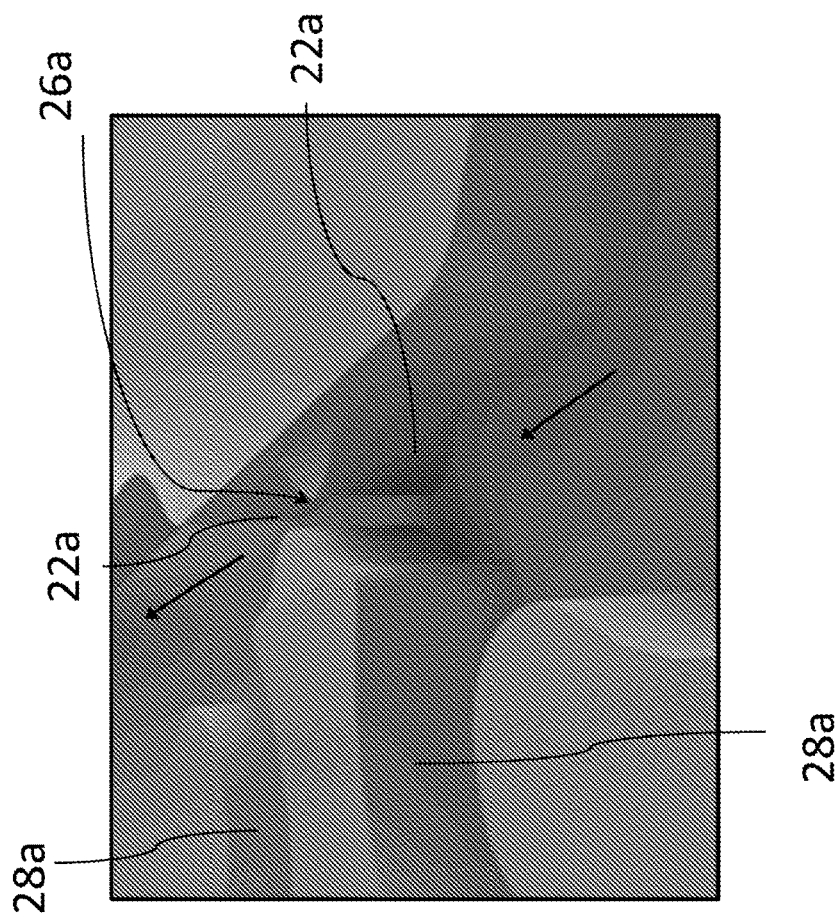
Figure 4B:
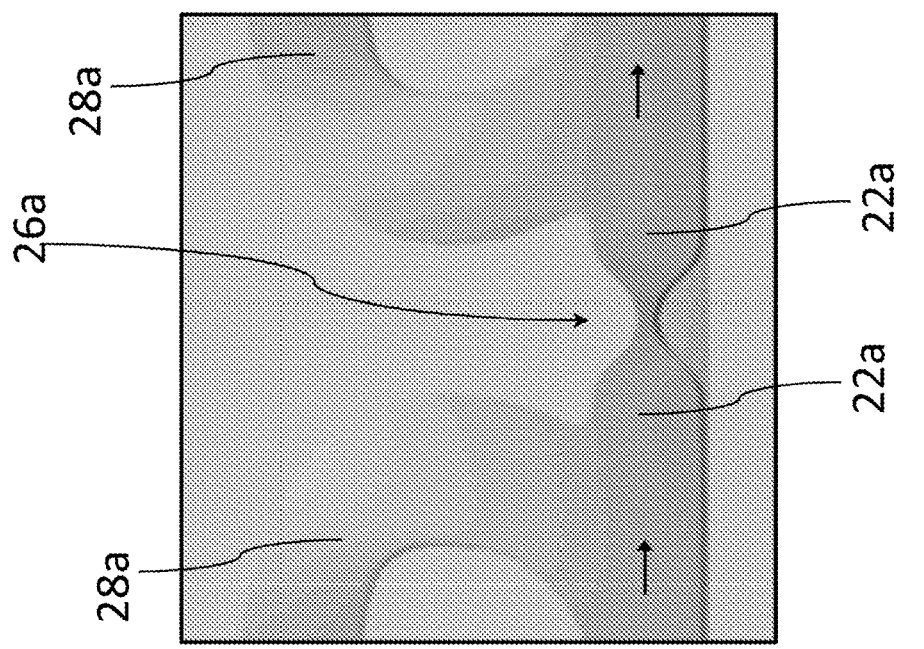

FIG. 4B is a plan view of a single trap in the microfluidic chip of FIG. 4A.

FIG. 4C is a perspective view of the single trap of FIG. 4B.

Figure 5:
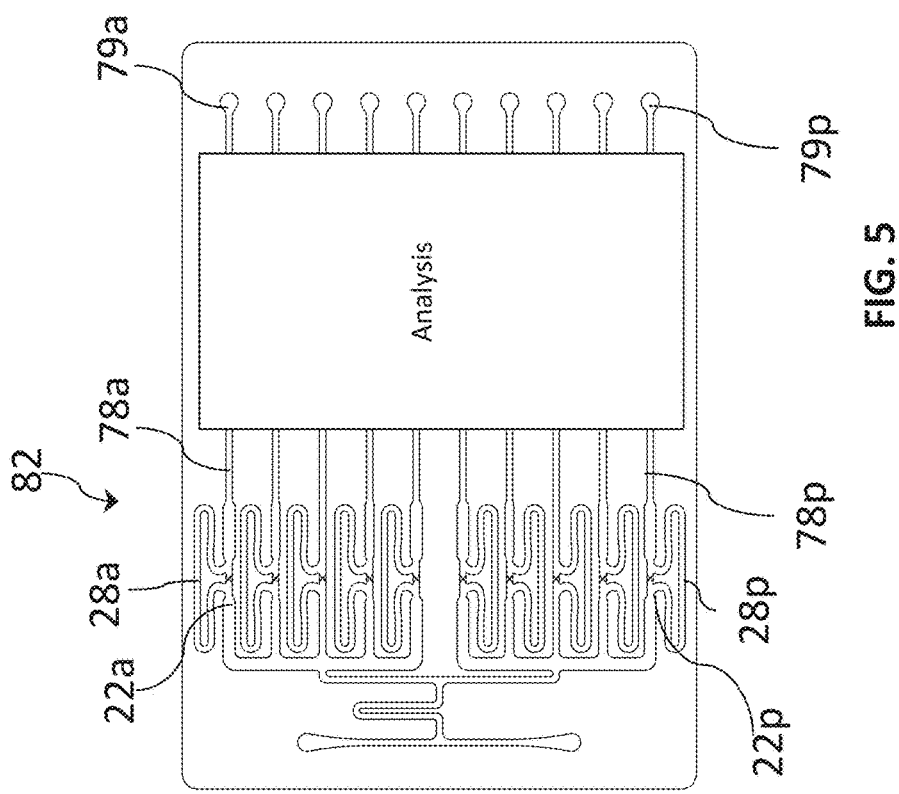

FIG. 5 is a plan view of a microfluidic chip including a bypass channel associated with each trapping channel and multiple output channels with each output channel connected to the combined output of a corresponding trapping channel and associated bypass channel in accordance with some embodiments.

Figure 6:
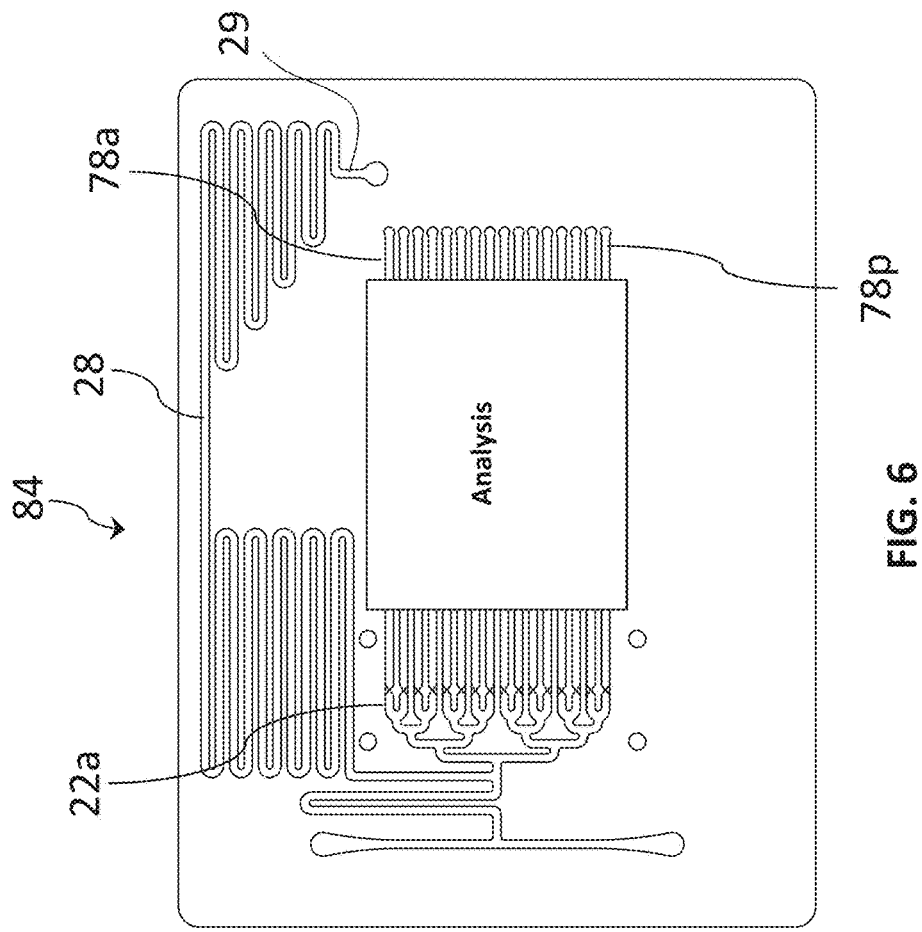

FIG. 6 is a plan view of a microfluidic chip including a single bypass channel and multiple output channels with each trapping channel having its own output channel in accordance with some embodiments.

FIG. 7 is a plan view of a microfluidic chip including two different trapping regions, one downstream of the other in accordance with some embodiments.

Figure 8:
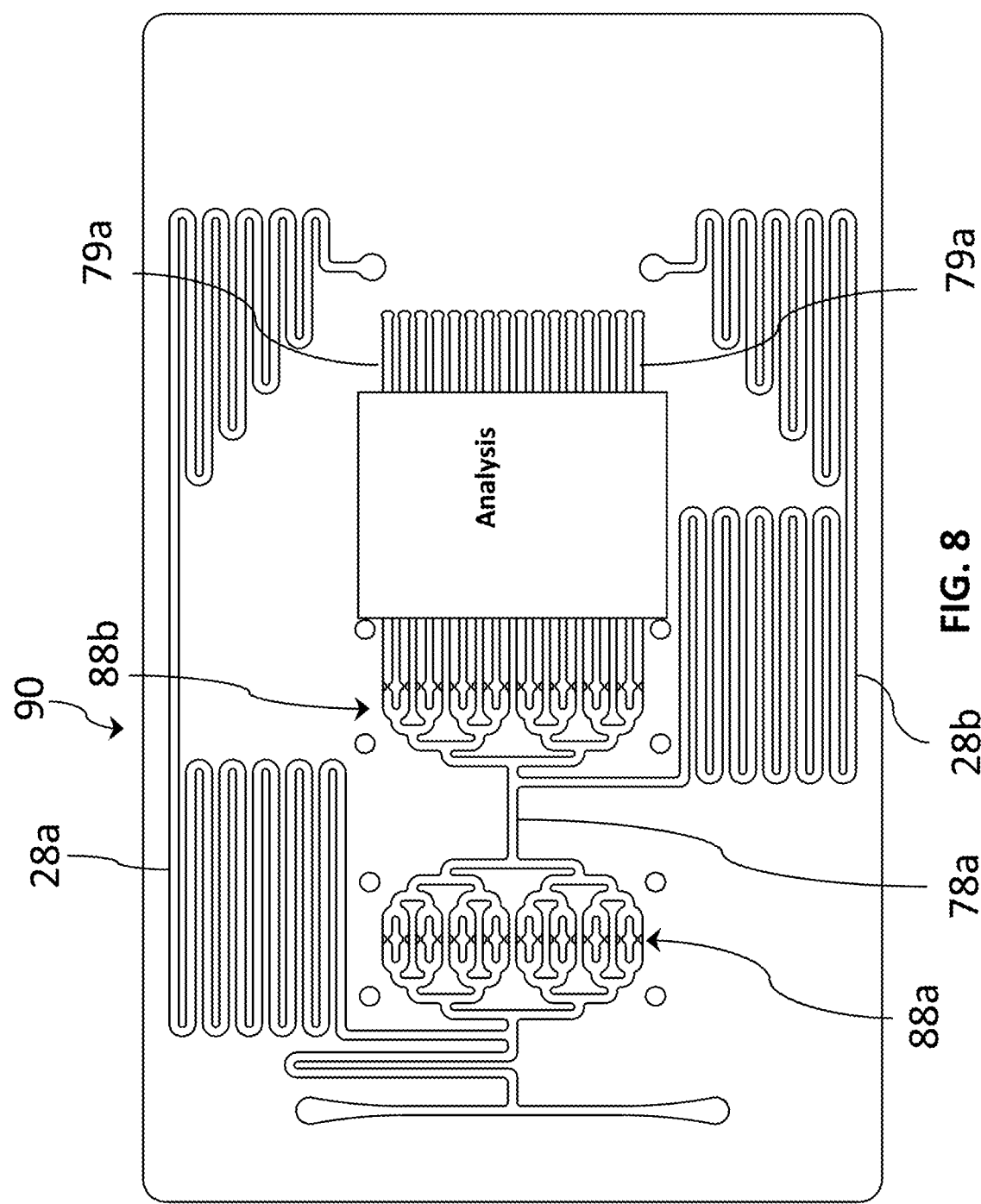

FIG. 8 is a plan view of a microfluidic chip including two different trapping regions, one downstream of the other where each trap in the second trapping region has its own dedicated output channel in accordance with some embodiments.

Figure 9:
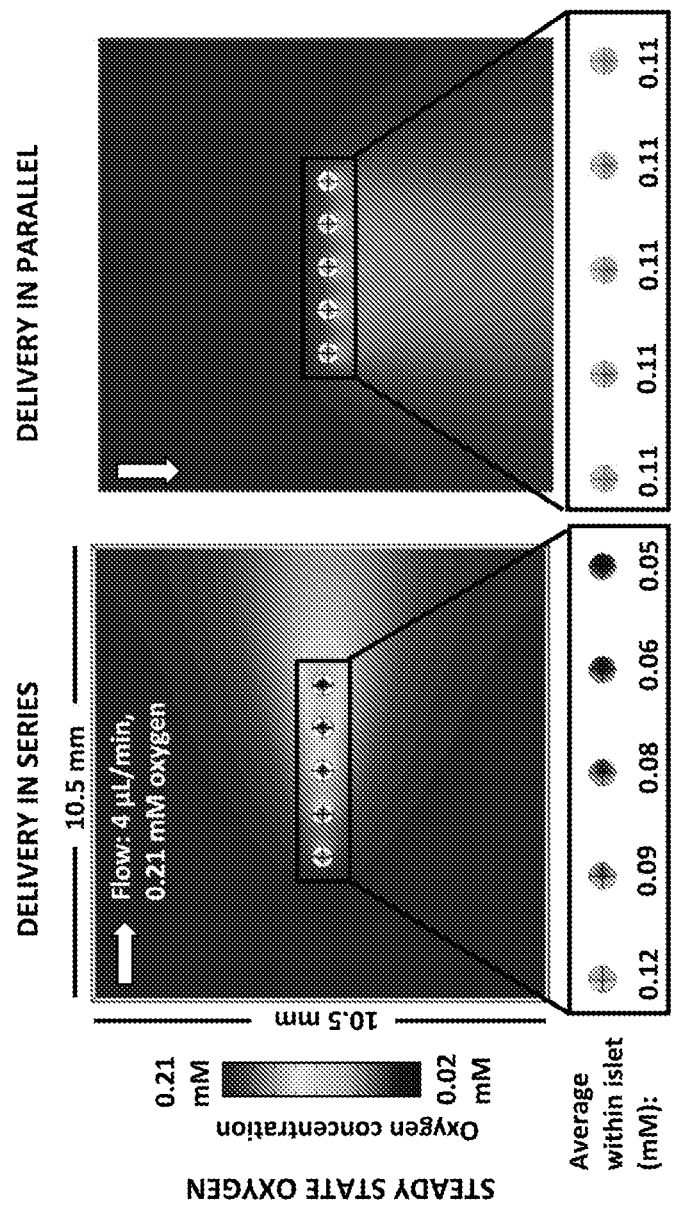

FIG. 9 includes images of results of a simulation showing concentrations of oxygen in a flow interacting with islet cell clusters where the clusters are arranged in series (left) and in parallel (right).

Figure 10:
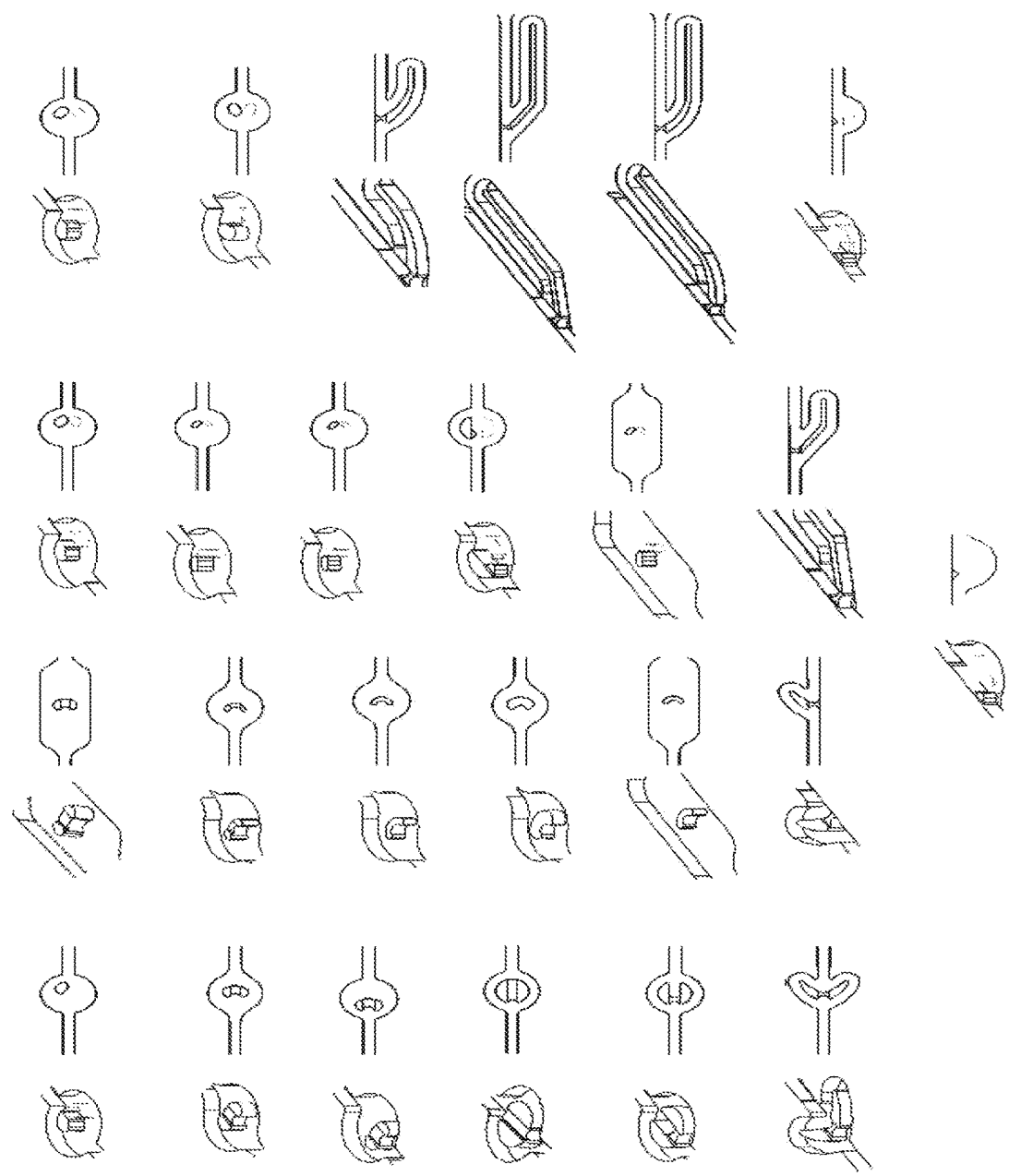

FIG. 10 includes drawings of different trap designs modeled and simulated.

Figure 11:
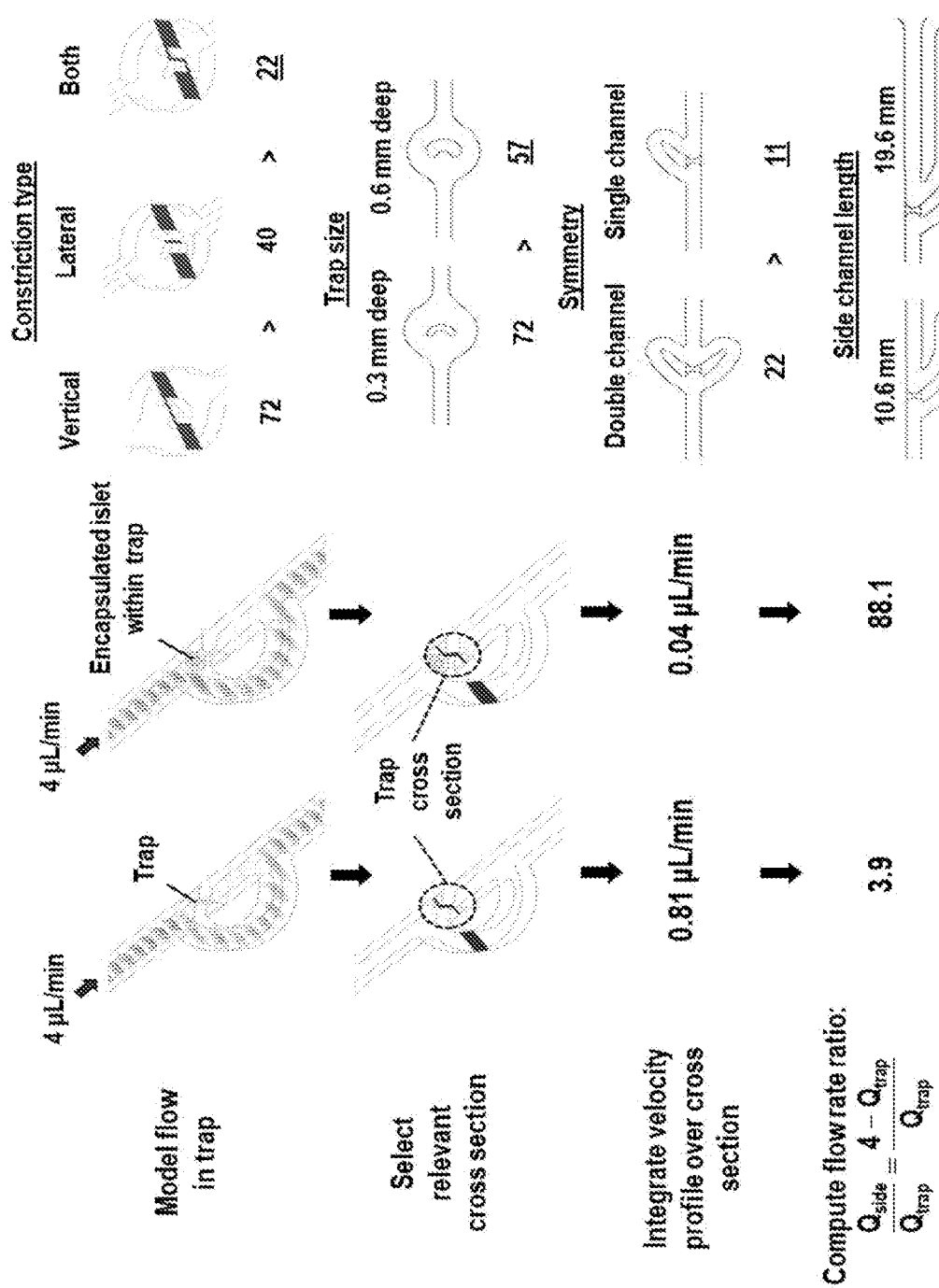

FIG. 11 schematically illustrates aspects of a simulation process for a trap design.

Figure 12:
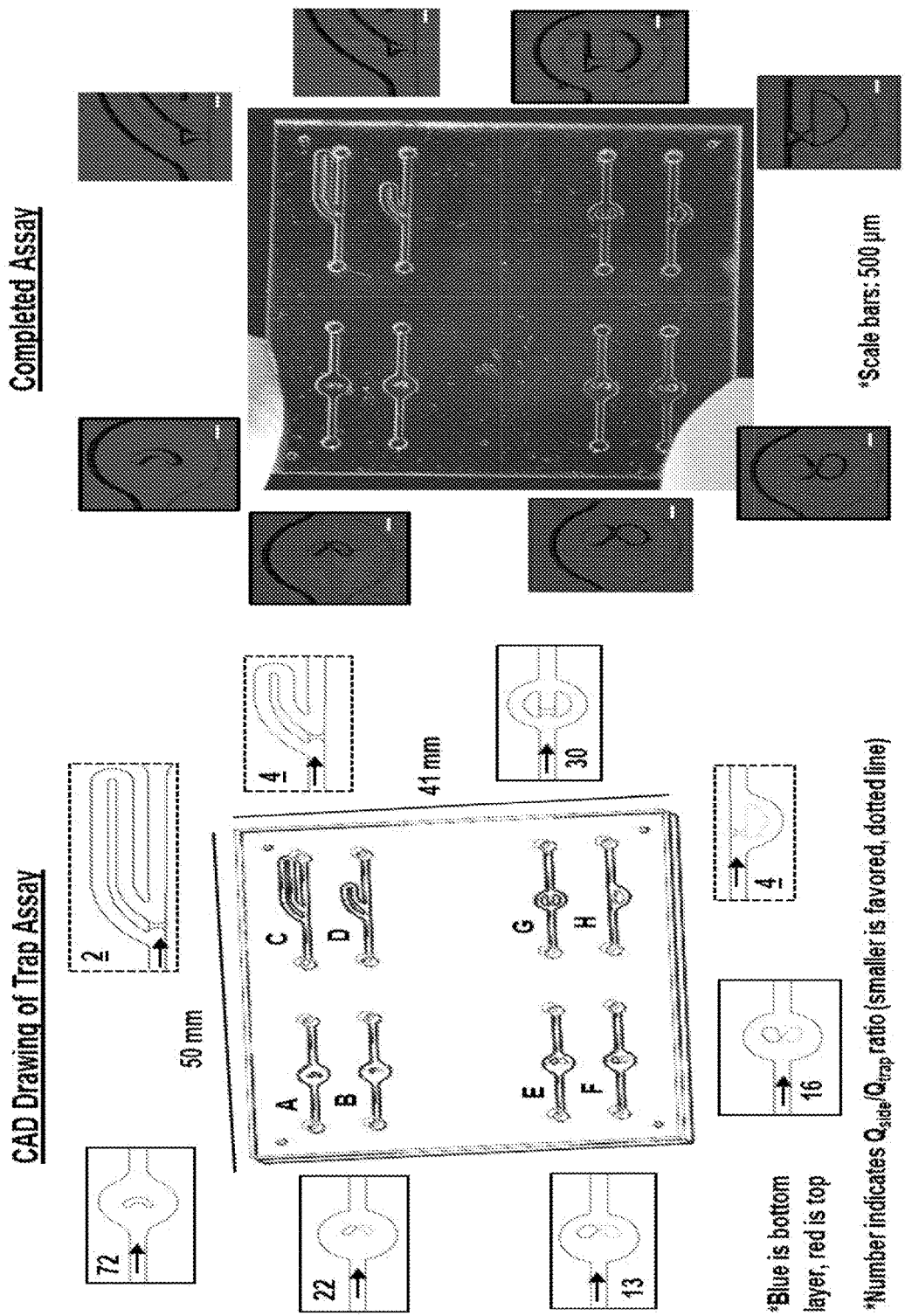

FIG. 12 includes a drawing of different trap designs (left) and an image of a prototype microfluidic chip used to test the different trap designs.

FIG. 13 includes images of clusters trapped in different traps of a prototype microfluidic chip described in Example 3.

Figure 14:
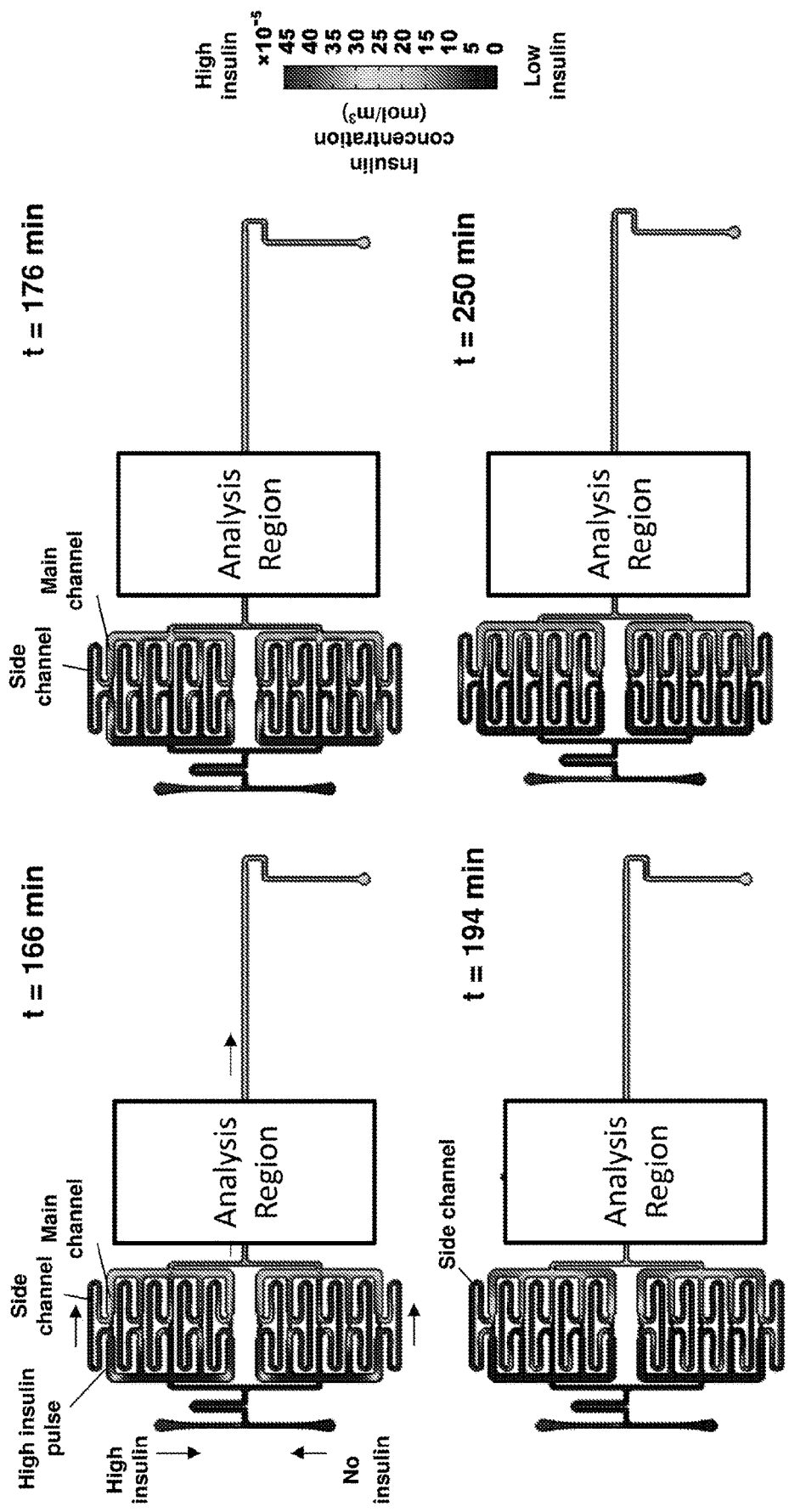

FIG. 14 depicts results of modeling of the propagation of a time dependent input through a microfluidic chip described in Example 3.

FIG. 15 includes an image and detail images of a prototype microfluidic chip produced and tested as described in Example 4.

Figure 16:
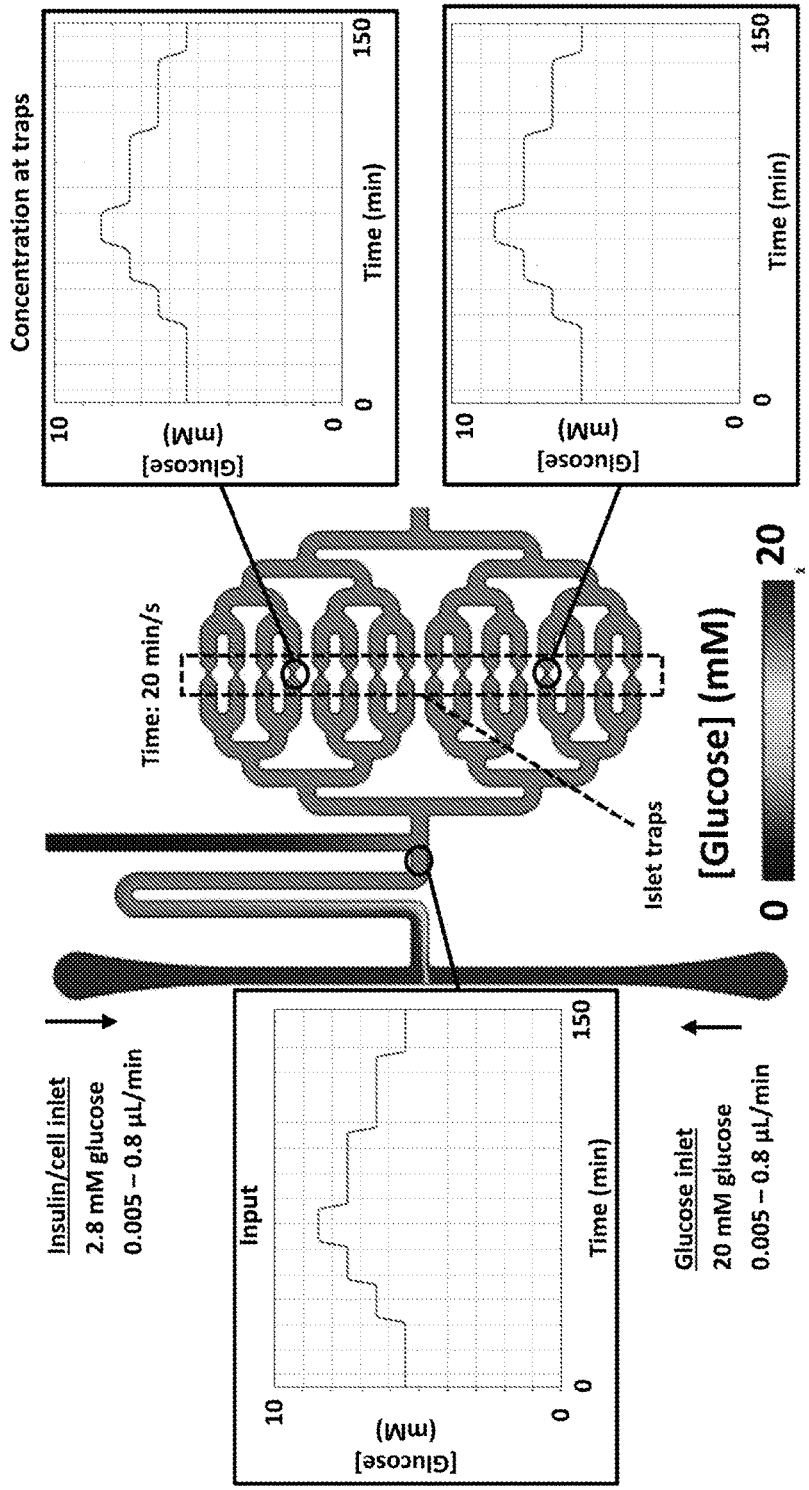

FIG. 16 is an image of results of modeling of the propagation of a time dependent input through the microfluidic chip described in Example 4.

FIG. 17 includes an image of bubbles that developed in trapping channels during use of the microfluidic chip of Example 4 and images of a modified chip that incorporated hydrophobic membranes for gas exchange as described in Example 5.

FIG. 18 depicts modeling used to determine a required mixing channel length.

Figure 19:
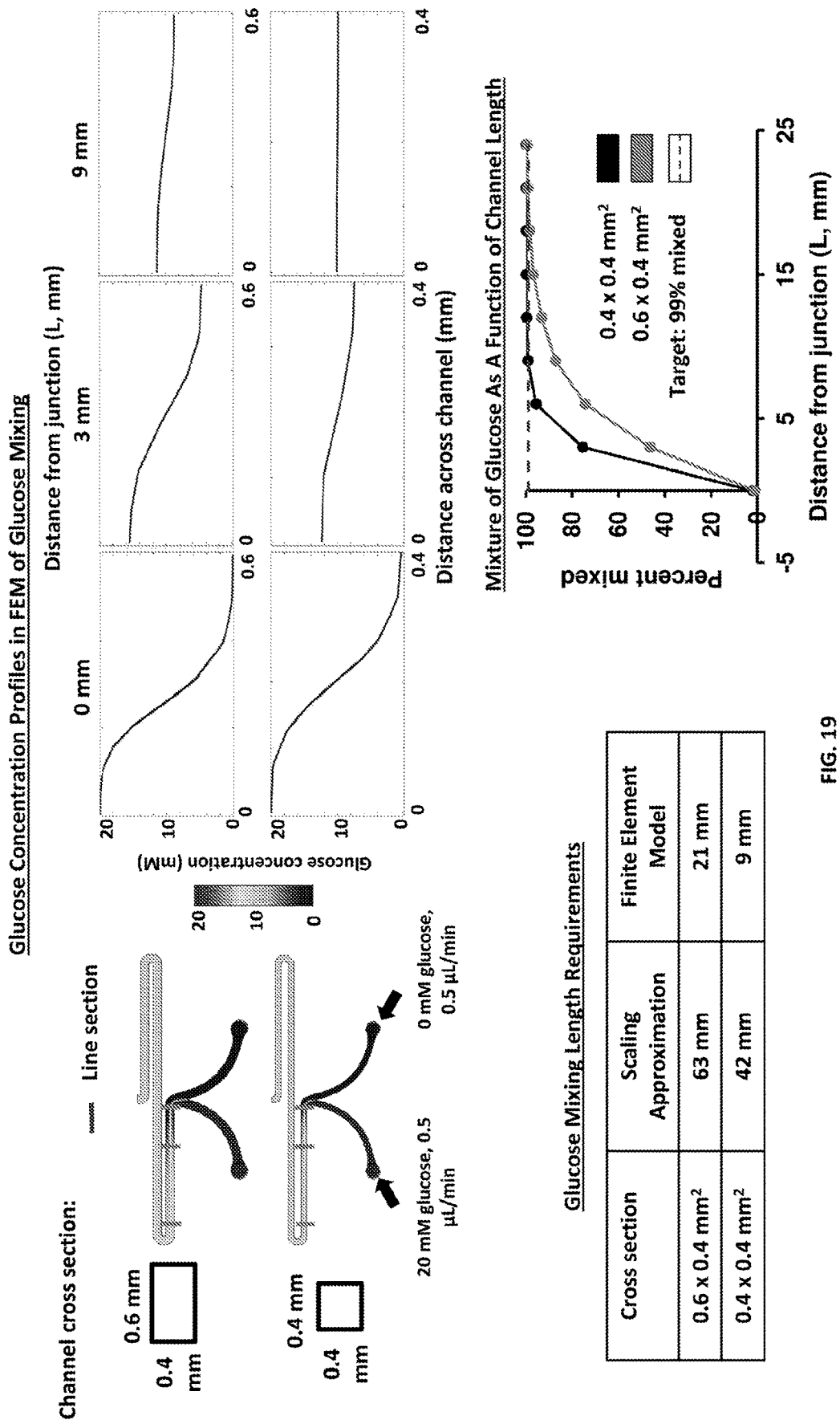

FIG. 19 shows the results of the modeling to determine a required mixing channel length.

DETAILED DESCRIPTION OF THE INVENTION

Some embodiments provide a microfluidic chip configured to automatically isolate and capture objects (e.g. islets, organoids, adipocytes, liposomes, microbeads) into their own designated and isolated traps in trapping channels, which can be used to deliver parallel and dynamic stimulation to the objects with chemicals. Analyte secreted by the trapped objects can be measured and analyzed in real time. Inspired by the designated blood flow to every islet in a human pancreas, hydrodynamic traps were designed to trap objects, where each trap contains a single object located in its own channel branching from an input channel for perfusion. In some embodiments, the flow path from an inlet to a trap has the same channel length and contains the same channel volume for each trap, ensuring synchronization of signals (e.g., flow input) delivered to the traps. In some embodiments, at least two inlets enable the delivery of dynamic chemical signals, where adjusting the relative flow rates of high and low concentrations of a stimulus introduced at each inlet generates an intermediate concentration.

Some embodiments provide a microfluidic chip that employs hydrodynamic loading of cell clusters and organoids into traps in parallel trapping channels that prevent cluster to cluster interactions and enable greater control over culture conditions for the clusters. In some embodiments, the microfluidic chip includes two or more inlets and one or more outlets. The two or more inlets can be connect to sources of medium of buffer with different concentrations of a stimulus of interest (e.g. glucose) so that the level of stimulus delivered to the cell clusters can be modulated dynamically by changing the relative ratio of flow rates from each source. In order to achieve adequate mixing, in some embodiments a channel downstream of the junction where these two inlets meet may have sufficient length for horizontal diffusion of the stimulus molecules from the multiple inlets prior to branching of channels for the trapping channels.

In an effort to facilitate loading of clusters, in some embodiments the microfluidic chip employs a hydrodynamic trapping structure to automatically capture a specific number of clusters. The structure uses channel geometries that preferentially direct flow through a trapping channel including a trap, specifically a constriction in the channel down to a lateral gap smaller than a cluster diameter. When a cluster attempts to travel through the trap, it becomes lodged in the constriction, trapping the individual cluster and partially blocking flow through the constriction. Due to the partial blockage of flow through the constriction, subsequent clusters are preferentially redirected into bypass channel that bypasses the trap.

In some embodiments, flow through one or more bypass channels can reduce the responsivity of the microfluidic chip to changes in a composition of input flow. In some embodiments, the microfluidic chip is configured such that flow through one or more bypass channels can be blocked after loading of the chip, to reduce or eliminate reduced responsivity due to bypass channel flow.

In some embodiments, some or all of the channels and traps of the microfluidic chips are formed by one or more recesses in a first surface of a first portion of a body in cooperation with a second surface of a second portion of the body having one or more projections. In some embodiments, the manufacturing process for the channels and traps includes attaching the first surface of the first portion of the body to the second surface of the second portion of the body (e.g., by fusing or thermal bonding). In some embodiments, the first portion and the second portion are configured to be mass produced by injection molding and/or hot embossing.

Some embodiments of microfluidic devices (e.g., microfluidic chips) are improvements over conventional technology for culturing clusters by facilitating seeding of clusters and setup of experiments. At the same time, the microfluidic devices enable control over the number, placement, and isolation of clusters to reduce variability for a given experiment. In some embodiments, hydrodynamic trapping enables capture of a defined number of clusters with minimal effort into traps in parallel trapping channels, while channels deliver parallel flow to ensure equal stimuli for all. In some embodiments, a simple, two-piece fabrication process—combined with the use of an optically-transparent thermoplastic material—also improves robustness and paves a path for large scale manufacturing.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

The term "comprising" or "comprises" is used herein in reference to compositions, methods, and respective component(s) thereof, that are essential to the disclosure, yet open to the inclusion of unspecified elements, whether essential or not.

The term "consisting of" refers to compositions, methods, and respective components thereof as described herein, which are exclusive of any element not recited in that description of the embodiment.

The term object, as used herein in conjunction with trapping channels and traps, includes any material or living thing, or combination of or more materials and one or more living things, that falls in the specified diameter range and is sufficiently solid to be trapped by a trap. An object can be or can include one or more cells. For example, the term object includes, but is not limited to a pancreatic islet, a hypertrophic adipocyte, a cell cluster, and a cell cluster conformally coated with a hydrogel. The term object need not include one or more cells. For example, the term object also includes a microsphere, e.g., a microsphere used for capture of proteins/cells/DNA.

The term trapping as used herein refers to an object being located in a trap upstream of a constriction in a corresponding trapping channel and unable to flow downstream beyond the constriction or out of the trapping channel when a flow within an intended pressure range for the chip is applied in an inlet to outlet flow direction. In some embodiments, objects may be "freed" or "recovered" from traps by reversing a flow direction in the microfluidic chip such that fluid flows from an outlet to an inlet, but this does not mean that the objects were not trapped when a flow in the inlet to outlet flow direction was applied. Further, an "empty" trap or an "unoccupied" trap means that an object in the specified diameter range is not located within the trapping channel upstream of the trap; however, an empty trap may still have liquid or objects smaller than a minimum trapping size flowing through it. The term "microfluidic chip" as used herein refers to a device having at least one channel with a diameter (length or width or lateral gap) on a sub-millimeter length scale. A microfluidic chip, as used herein, is a device that is substantially or fully integrated into a single unit, as opposed to being several different units that are connected to each other via tubing or wires.

Some embodiment will be described herein for simplicity with respect to the trapping of objects that are or include one or more cells (e.g., cell clusters or organoids). However, one of ordinary skill in the art in view of the present disclosure will appreciate that microfluidic chips and methods described herein can be employed with other types of objects including cells, or with objects that do not include cells.

It should be understood that the relative terminology used herein, such as "front", "rear", "left", "top", "bottom", "base", "vertical", "horizontal", "upward" and "downward" is solely for the purposes of clarity and designation and is not intended to limit the invention to embodiments having a particular position and/or orientation. Accordingly, such relative terminology should not be construed to limit the scope of the present invention. In addition, it should be understood that the invention is not limited to embodiments having specific dimensions. Thus, any dimensions provided herein are merely for an exemplary purpose and are not intended to limit the invention to embodiments having particular dimensions. In addition, different embodiments of the exemplary fluidic systems are described herein. However, certain structural elements of the different embodiments can be substantially similar in structure and/or function. As such, similar reference numbers are used herein to refer to similar structures.

II. Devices of the Invention

FIGS. 1A to 2A depict a microfluidic device, specifically, a microfluidic chip 10, that employs hydrodynamic trapping of objects (e.g., cell clusters or organoids) in traps disposed in trapping channels that are parallel with respect to each other. The parallel trapping channel geometry enables improved control over conditions to which the objects (e.g., cell clusters or organoids) are exposed, and reduces or prevents object to object interactions for the trapped objects (e.g., prevents cell to cell interactions between cells in different cells clusters or different organoids). For simplicity, in some places, the microfluidic chip 10 will be described below with respect to trapping of objects that are cell clusters; however, one of ordinary skill in the art in view of the present disclosure will appreciate that the objects need not be cell clusters and need not include cells.

The microfluidic chip 10 includes a body 12. In some embodiments, the body comprises a polymer such as a thermoplastic polymer (e.g., polycarbonate). The body 12 includes one or more inlets (e.g., first inlet 14 and second inlet 16). In some embodiments the body includes two or more inlets that enable dynamic control of a composition of a fluid supplied to the microfluidic chip by connecting fluids sources having different compositions to the two inlets and dynamically changing relative amounts fluid supplied by each fluid source over time. The body 12 also includes one or more outlets (e.g., outlet 18 and bypass outlet 20).

The body also includes a plurality of trapping channels 22a-22p in parallel with each other (see FIGS. 1A and 1B). The plurality of trapping channels 22a-22p each connect with at least one of the one or more inlets in an upstream directions and with at least one of the one or more outlets in a downstream direction. In microfluidic chip 10, each of the trapping channel 22a-22p connects to both inlets 14 and 16 through connecting channels in an upstream direction in accordance with some embodiments. In microfluidic chip 10, each of the trapping channels 22a-22p connects to outlet 18 in a downstream direction through one or more channels, in accordance with some embodiments. In some embodiments, an output from the microfluidic chip such as from outlet 18 may be employed for analysis using another chip, device or assay. In some embodiments, analytics may be incorporated into chip 10, and one or more flows from the plurality of trapping channel may be directed to an analysis region 24 of the microfluidic chip prior to exiting via the outlet 18.

Each trapping channel includes a hydrodynamic trap 26a-26p configured to trap an object having a diameter in a specified sub-millimeter range. In some embodiments, the specified sub-millimeter range falls in a range of 10 microns to 1 mm. In some embodiments, the specified sub-millimeter range falls in a range of 70 microns to 400 microns. In some embodiments, the specified sub-millimeter range includes 80 microns to 350 microns. In some embodiments, the specified sub-millimeter range includes 100 microns to 300 microns. In some embodiments, the specified sub-millimeter range includes 80 microns to 200 microns. In some embodiments, the specified submillimeter range falls in a range of 10 microns to 100 microns. In some embodiments the specified submillimeter range includes 10 microns to 30 microns. Further description of the structure of the traps is provided below with respect to FIGS. 1E and 1F.

The microfluidic chip 10 includes a bypass channel 28 arranged in parallel with and associated with at least one of the plurality of trapping channel 22a-22p. In the embodiment depicted in FIGS. 1A-2B, the bypass channel 28 is arranged in parallel with and associated with all of the plurality of trapping channels 22a-22p. An upstream end of the bypass channel 28 is connected with at least one of the one or more inlets. In the depicted embodiment, the bypass channel 28 is connected with both inlets 14 and 16. A downstream end of the bypass channel 28 connects with at least one of the one or more outlets. In the depicted embodiment, bypass channel connects to bypass outlet 20.

The bypass channel 28 and the associated plurality of trapping channels 22a-22p are configured such that an object (e.g., a cell cluster) in a fluid introduced through inlet 14 and/or inlet 16 that flows into a channel 19 directly upstream of the bypass channel preferentially flows into an empty trap 24a-24p of the plurality of trapping channels 22a-22p when there is an empty trap, and such that the object (e.g., a cell cluster) preferentially flows into the bypass channel 28 when none of the traps 24a-24p of the associated trapping channels is empty. This enables automatic or automated hydrodynamic loading of single objects (e.g., cell clusters) into each trap for multiple different traps. An explanation of how the microfluidic chip 10 achieves this hydrodynamic trapping and different embodiments for such hydrodynamic trapping is provided below with respect to Examples 2-4.

Channels leading to the traps 22a-22p are configured such that trapped clusters receive parallel delivery of flow from the one or more inlets 14, 16. In conventional designs where some clusters are arranged downstream of other clusters in series, the composition of the flow received by downstream clusters can be affected by the upstream clusters and there can be cell to cell interactions between different clusters (see discussion of parallel versus series flow for islets in Example 1). Further, with clusters arranged in series, different clusters are exposed to the flow at different times, which may be undesirable if measuring effects having a short time scale. In some embodiments the microfluidic chip 10 is arranged such that a flow delivered to one or more of the inputs reaches the traps at about the same time or simultaneously. For example, in microfluidic chip 10, the configuration of the multi-tiered branching channel structure (e.g., first tier of branches 30a, second tier of branches 30b, third tier of branches 30c in FIG. 1B) upstream of the trapping channels is such that a flow path distance from the inlets 14, 16 to the trap 24a-24p is the same for every trap 24a-24p This configuration ensures that traps receive the same input simultaneously.

Some embodiments do not have the same flow path lengths from the inputs to the trap for each trap, but instead use other configurations to ensure simultaneous delivery of the same input to each trap. For example, some embodiments that don't employ such a tiered branching structure upstream of the trapping channels but instead have each trapping channel branching directly off of the same upstream channel, peripheral channels may be wider to account for the additional flow path length, ensuring that the resistance to flow is equivalent in all trapping channels when the traps are empty.

In some embodiments, the input from two or more inlets 14, 16 are combined in a mixing channel 31 that connects with the two inlets 14, 16 upstream of the plurality of trapping channels 22a-22p. In some embodiments, the channel 19 directly upstream of the bypass channel is also the mixing channel 31. In some embodiments, a length of the mixing channel is configured such that input fluid from the at least two inlets mixes via lateral diffusion of components of the input fluid prior to reaching the plurality of trapping channels 22a-22p (see discussion of Example 6 below).

In some embodiments, an output of the bypass channel flows to a different outlet from the output of the trapping channels. For example, in microfluidic chip 10, the bypass channel flows to outlet 20 and flow from the trapping channels flow to a different outlet 18. This enables the bypass channel 28 to be selectively blocked to reduce or stop flow into the bypass channel 28 after completion of loading of the microfluidic chip. In some embodiments, flow through one or more bypass channels can reduce the responsivity of the microfluidic chip to changes in a composition of input flow as explained below with respect to Example 3. Configurations that enable selective blocking of the bypass channel after loading may reduce or prevent flow in the bypass channel from detrimentally affecting the responsivity of the microfluidic chip to changes in a composition of input flow.

Physical features of traps in some embodiments are explained with respect to FIGS. 1C to 1F below. In some embodiments, at the trap 24a, 24p, a width ($w_o$) of the trapping channel 22a, 22p is reduced to a narrower lateral trap width ($w_t$) which may also be referred to as a lateral gap width ($g_{t1}$, $g_{t2}$) over at least a portion of a height of the trapping channel as illustrated in FIGS. 1C and 1D.

In some embodiments, the trapping channel has a first sidewall 32, a second sidewall 34 opposite the first sidewall, a base surface 36, and a top surface 38 opposite the base surface. The top surface is not visible in FIGS. 1C through 1E, but is schematically depicted in the cross-section of FIG. 1F. One of ordinary skill in the art will understand that the selection of which surface is labeled the base surface and which surface is labeled the top surface is arbitrary and the microfluidic chip could be used in an orientation where the base surface is above the top surface. The trapping channel 22p includes a first protrusion 40 of the first sidewall 32 extending from the base surface 36 toward the top surface 38 of the trapping channel 22p with the first protrusion 40 having a height less than a maximum height $h_m$ of the trapping channel forming a first shelf 42 with a top gap $g_{t1}$ separating the shelf 42 from the top surface 38. The trapping channel 22p also includes a second protrusion 44 of the second sidewall 34 extending toward the first sidewall 32 and extending from the top surface 38 toward the base surface 36, with the second protrusion having a height less than the maximum channel height $h_m$ forming an overhang 46 with a bottom gap $g_{b1}$ separating the overhang 46 from the base surface 36 of the trapping channel 22p. The second protrusion 44 is disposed opposite the first protrusion 40 such that a lateral gap $g_{t1}$ separates the first protrusion 40 and the second protrusion over at least a portion of the height of the channel. The narrowing of the trapping channel 22p at the lateral gap formed by the first protrusion 40 and the second protrusion 44 is configured to trap an object, and the top gap formed by the shelf 42 and the bottom gap formed by the overhang 46 are configured to enable some fluid to flow through the trapping channel 22p around the trapped object (e.g., above and below the trapped object) while still keeping the object trapped.

In some embodiments, the trapping channels are paired. As shown in FIGS. 1D-IE, trapping channel 22p is paired with trapping channel 22o, which has a trap 26o. Trapping channel 22o has a base surface 36 and a top surface 38, a third sidewall 48 and a fourth sidewall 50. The third sidewall 48 includes a third protrusion 52 extending from the base surface 26 toward the top surface 38 and having a height less than a maximum height $h_m$ of the trapping channel 22p forming a second shelf 54 with a second top gap $g_{b2}$ separating the second shelf 54 from the top surface 38 of the trapping channel 22o. The fourth sidewall 50 includes a fourth protrusion 56 extending from the top surface 38 toward the base surface 36 of the trapping channel 22o with the fourth protrusion 56 having a height less than the maximum height $h_m$ of the trapping channel 22o forming a second overhang 58 with a second bottom gap $g_{t2}$ separating the second overhang 58 from the base surface 36. The narrowing of the trapping channel 22o at the lateral gap formed by the third protrusion 52 and the fourth protrusion 56 is configured to trap an object, and the top gap formed by the second shelf 54 and the bottom gap formed by the second overhang 58 are configured to enable some fluid to flow through the trapping channel 22o around the trapped object (e.g., above and below the trapped object) while still keeping the object trapped.

In some embodiments the body comprises a first portion 60 including a first surface 62 including one or more recesses 64, and a second portion 66 attached to, coupled to, or fused with the first portion 60. A second surface 68 of the second portion has one or more projections 70. The one or more recesses 64 of the first surface 62 of the first portion 60 and the one or more projections 70 of the second surface 68 of the second portion cooperating to define traps of the plurality of trapping channels. For example, the projection 70 in FIG. 2C and the recess 64 in FIG. 2B cooperate to define trapping channels 22p and 22o and corresponding traps 26p and 26o in FIGS. 1D and 1E. In some embodiments, the first sidewall 32, the first protrusion 40, and the shelf 42 are formed by a recess 64 in the first surface of the first portion 60 and the second sidewall 34, the second protrusion 44, the and the overhang 46 are formed by the projection 70 of the second surface of the second portion 66. In some embodiments, the third sidewall 48, the third protrusion 52 and the second shelf 54 are also formed by the same recess 64 as depicted in FIGS. 1E-2C. In some embodiments, the fourth sidewall 50, the fourth protrusion 56, the and second overhang 58 are formed by the same projection 70 as depicted in FIGS. 1E-2C.

In some embodiments, all the trapping channels 22a-22p and traps 26a-26p of the microfluidic chip 10 are formed by one or more recesses 64 in the first surface 62 of the first portion 60 and one or more projections 70 in the second surface 68 of the second portion 66.

In some embodiments a shape of the one or more recesses 64 is consistent with being formed by machining, injection molding or embossing of a single piece. In some embodiments, a shape of the one or more projections 70 is consistent with being formed by machining, injection molding of embossing of a single piece.

In some embodiments, the first portion 60 comprises a thermoplastic and the second portion comprises a thermoplastic 66. In some embodiments the first portion bonded to or fused with the first portion to form the trapping channels.

In various embodiments, one or more hydrophobic membranes may disposed between the first and second portions of the device to define an interface between liquid in a channel below the membrane and air in a channel or hole above the membrane. A hole would be cut through the entire thickness of the second portion of the device, whereas a channel would be a partial recess in the second surface of the second portion of the device that connects to an air hole. Air holes and channels are intended to be placed over channels in the device to create the liquid-gas interface separated by the membrane.

The membranes allow for gas exchange between the liquid on one side of the membrane and the gas phase on the other side. In some embodiments, this enables for removal of bubbles that might form inside the stream of liquid. In some embodiments this configuration enables delivery of a specific gas (such as oxygen) to the liquid flowing in the microfluidic device.

In the latter case, a membrane can be dimensioned so that it fits over the entire trapping region. To do so, holes that allow for the projections from the second portion to meet the recess in the first portion must be made in the shape of those projections. In some embodiments, this can be accomplished with a laser cutter. In some embodiments, alignment posts that fit through holes on the periphery of the membrane can be used to properly position the membrane. These alignment posts would be projections from the second surface of the second portion of the device. The posts would fit through the holes in the membrane and fit into recesses on the first surface of the first portion of the device. A similar alignment scheme of posts and holes can be used to help align the trap features (i.e. the projections and recesses) on the first and second portions of the device.

As illustrated in FIGS. 3A-3D, in some embodiments, a microfluidic chip 11 includes one or more hydrophobic membranes disposed between the first portion 66 and the second portion 60 and the second portion 62. The one or more hydrophobic membranes 72 overly one or more of: at least a portion of a recess in the first portion corresponding to an inlet channel connected to at least one of the one or more inlets; at least a portion of a recess in the first portion corresponding to a mixing channel 31; and at least a portion of a recess 64 in the first portion corresponding to the plurality of trapping channels 22a-22p. The hydrophobic membranes enable gas to pass through, but prevent liquid from passing through the membrane. In some embodiments, the second portion 66 of the body includes one or more holes 74 each extending through the second surface 68 the second portion where one of the hydrophobic membranes 72 is overlying a recess corresponding to a channel. In some embodiments, each hole enables 74 gas that passes from the channel underlying the hydrophobic membrane and through the hydrophobic membrane 72 to exit the microfluidic chip 11. In some embodiments, this prevents the buildup of gas bubbles in the microfluidic chip during long term culture. In some embodiments, at least one of the one or more holes 74 is configured to be connected to a source of gas for delivery for delivery of a gas or a component of the gas through the hydrophobic membrane 72 and into the channel underlying the hydrophobic membrane. For example, gas supplied through the one or more holes 74 could be employed for oxygenation of fluid passing below the hydrophobic membrane 72. Gas exchange can occur in both directions depending on the concentration gradient applied. In some embodiments, the second surface 68 of the second portion 66 includes a groove 76 that overlays at least a portion of the channel underlying the hydrophobic membrane 72, where the groove 76 and the hydrophobic membrane 72 for a gas channel for the flow of gas between the at least one hole 74 and the hydrophobic membrane 72, as depicted in FIGS. 3B-3D.

The inclusion of the hydrophobic membranes 74 may put limitations on an input fluid pressure supplied to the microfluidic chip 11 as at high input fluid pressures liquid may seep through the hydrophobic membrane 74. Accordingly, in some embodiments, no hydrophobic membrane is employed.

In some embodiments, the first portion 60 and the second portion 62 include features for alignment, such as alignment posts 92 in the second portion 66 (see FIG. 3C) that are received by with corresponding alignment recesses in the first portion. In some embodiments, the second portion includes through holes providing portion for the inlets. In some embodiments, an outward facing surface of the second portion is shaped to provide inset barbs such that elastic tubing can be attached to the port.

In some embodiments, a microfluidic chip may include multiple bypass channels instead of a single bypass channel. For example, FIGS. 4A-4C depicts a microfluidic chip 80 in which each trapping channel 22a-22p has its own associated bypass channel 28a-28p.

As shown in FIGS. 4B and 4C, the associated bypass channel 28a branches directly off the trapping channel 22a immediately before the trap 26a. In this embodiment, the bypass channels cannot be selectively blocked after loading of the cells. The applicants determined that this configuration of bypass channels reduced the temporal sensitivity of the microfluidic chip to changes in input flow at the traps as explained below with respect to Example 3.

In this particular embodiment, the output from all the trapping channels 22a-22p and all the bypass channels 28a-28p is combined into a single output 78. However, other embodiments may include other numbers of output channels and other configurations of output channels. In addition to the embodiments described previously, both single bypass channel embodiments of the microfluidic chip and embodiments with a bypass channel for each trap can be configured such that the trapping channels downstream of the traps converge to a single output (pooling the outflow from these traps), such that the outflow of subgroups of the trapping channels converge, or such that each trap has have its own dedicated outlet to enable for individual analysis of what each trapped object is releasing/producing.

For example microfluidic chip 82 of FIG. 5 is similar to microfluidic chip 80 of FIGS. 4A-4C, except that each trapping channel 22a-22p and associated bypass channel combination has its own output channel 78a-78p and its own outlet 79a-79p. As another example, microfluidic chip 84 of FIG. 6 is similar to microfluidic chip 10 of FIGS. 1A-1F, except that each trapping channel 22a-22p has its own output channel 78a-78p enabling individual analysis of the output of each trap. Bypass channel 28 has its own bypass output 29.

Some embodiments include multiple trapping regions on the same microfluidic chip or device, with an outflow downstream of one or more trapping channels in a first trapping region feeding into a second trapping region. Using a single bypass channel design, one can duplicate the bypass and trapping motifs such that the trapping region of one flows towards a junction of the trapping region and bypass channel of another. The number of traps in each region can be different, and the trap sizes and shapes can be configured to capture objects in different size ranges. In order to ensure proper function, the traps upstream must be dimensioned to be large enough to allow objects for downstream capture through their respective constrictions. Otherwise, the objects intended for collection downstream will become trapped in an upstream trap. To capture multiple objects, one would sequentially add in suspensions of the smallest objects up to the largest objects. At each trapping stage, all bypasses channels but the bypass channel corresponding to the target trapping region would be blocked, such that the objects will flow through the upstream traps until they reach the split in channels leading either to the target trapping region or its corresponding bypass.

For example, microfluidic chip 86 includes a first trapping region 88a including a first plurality of trapping channels and a first bypass channel 28a, and a second trapping region 88b downstream of an combined output 78a of the first plurality of trapping channels. The second trapping region including a second plurality of trapping channels and a second bypass channel 28b. The output of the second plurality of trapping channels 88b in the second trapping region 88b combined into a single output 78b. As another example, microfluidic device 90 is similar to microfluidic device 86, except that each trapping channel in the second plurality of trapping channels 88b has its own outlet 7aa-79p.

Such devices having different trapping regions could be used to analyze, for instance, the effect of pancreatic islet secretions on adipocytes captured further downstream, or the effect of drug microspheres on tumor organoids downstream in some embodiments.

In some embodiments, the microfluidic chips are configured to efficiently and effectively traps objects including cells at flow rates that are sufficiently low that the cells will not be damage by contact with the trap during loading. For example in some embodiments, the microfluidic chips are configured such that an object flowing through the microfluidic chip has a flow velocity of less than 5 mm/s directly upstream of the trap. If configured for use with using microbeads or other objects not including cells, the microfluidic chip could be configured for efficient and effective loading such that the objects have higher flow rates directly upstream of the trap.

III. Methods of Making Microfluidic Chip Devices

Some embodiments of methods of making a microfluidic chip are described using reference numbers employed for microfluidic chips described above solely for illustrative purposes. One of ordinary skill in the art in view of the present disclosure will appreciate that methods described herein can be used to make any and all the embodiments of microfluidic chips described herein.

A method of making a microfluidic chip includes forming the first portion 60 of the body 12 of the microfluidic chip having the one or more recesses 64 and forming the second portion 66 of the body having the one or more projections 70. The method also includes attaching, coupling or fusing at least a portion of the first surface 62 of the first portion 60 to at least a portion of the second surface 68 of the second portion 66, where the one or more recesses 64 of the first portion and the one or more projections 70 of the second portion cooperate to define the traps 26a-26p of the plurality of trapping channels 11a-22p. In some embodiments, one or both of the first portion 60 and the second portion 66 are formed by injection molding of a thermoplastic material. In some embodiments one or both of the first portion 60 and the second portion 66 are formed by hot embossing of a thermoplastic material. In some embodiments, one or both of the first portion 60 and the second portion 66 are formed by machining of a polymeric material.

In some embodiment, the first portion is bonded to the second portion using heat and pressure. In some embodiments, the first portion is fused to the second portion.

In some embodiments, one or more membranes are disposed between the first portion and the second portion before the first and second portions are joined, attached, coupled or fused.

IV. Methods of Using Microfluidic Chips

Some embodiments provide methods of using microfluidic chips. For example, an embodiment includes a method of loading and culturing cells. The method includes providing a microfluidic chip as described herein. The method further includes delivering fluid including objects each including one or more cells into one of the one or more inlets of the microfluidic chip and hydrodynamically trapping an object including one or more cells in each trap. The method also includes delivering a cell culture medium to the microfluidic chip to culture the one or more cells of each object in the traps. In some embodiments, the method includes blocking an outlet of the bypass channel of the microfluidic chip after hydrodynamically trapping the objects.

Another embodiment provides a method for identifying a cell differentiation, cell viability, and/or cell function. The method includes providing a microfluidic chip as described herein. The method also includes delivering fluid including objects each comprising one or more cells into one of the one or more inlets of the microfluidic chip and hydrodynamically trapping an object comprising one or more cells in each trap. The method further includes contacting the trapped objects with a test compound and determining the effect of the test compound on cell differentiation, cell viability, and/or cell function in the presence and absence of the test compound. A modulation of cell differentiation, cell viability, and/or cell function in the presence of said test compound as compared to cell differentiation, cell viability, and/or cell function in the absence of said test compound indicates that said test compound modulates cell differentiation, cell viability, and/or function, thereby identifying a compound that modulates cell differentiation, cell viability, and/or function.

Another embodiment provides a method for identifying a compound useful for treating a disease or disorder. The method includes providing a microfluidic chip as described herein. The method also includes delivering fluid including objects each comprising one or more cells into one of the one or more inlets of the microfluidic chip and hydrodynamically trapping an object comprising one or more cells in each trap. The method further includes contacting the trapped objects with a test compound and determining the effect of the test compound on cell differentiation, cell viability, and/or cell function in the presence and absence of the test compound. A modulation of cell differentiation, cell viability, and/or cell function in the presence of said test compound as compared to cell differentiation, cell viability, and/or cell function in the absence of said test compound indicates that said test compound modulates cell differentiation, cell viability, and/or function, thereby identifying a compound that useful for treating the disease or disorder.

In some embodiments, the objects include pancreatic islet cells, and the effect of the test compound on pancreatic islet cell viability and/or function in the presence and absence of the test compound is determined. In some embodiments, the disease or disorder is diabetes, the objects comprise pancreatic islet cells, and the effect of the test compound on pancreatic islet cell viability and/or function in the presence and absence of the test compound is determined.

Another embodiment provides a method for identifying a compound useful for treating diabetes. The method includes providing a microfluidic chip as described herein. The method also includes delivering fluid including objects each comprising pancreatic islet cells into one of the one or more inlets of the microfluidic chip and hydrodynamically trapping an object comprising the pancreatic islet cells in each trap. The method also includes determining the effect of the test compound on pancreatic islet cell viability and/or function in the presence and absence of the test compound. A modulation of pancreatic islet cell viability and/or function in the presence of said test compound as compared to pancreatic islet cell viability and/or function in the absence of said test compound indicates that said test compound modulates pancreatic islet cell viability and/or function, thereby identifying a compound useful for treating diabetes.

In one embodiment, the objects include adipocytes and the effect of the test compound on adipocyte differentiation, viability and/or function in the presence and absence of the test compound is determined. In one embodiment, the disease or disorder is lipodystrophy, the objects include adipocytes, and the effect of the test compound on adipocyte differentiation, viability and/or function in the presence and absence of the test compound is determined.

Suitable cells or cell clusters for use in the methods of the invention for identifying a compound useful for treating a disease or disorder include cells known to be affected by or associated with the disease or disorder. For example, in the case of a muscle disease or disorder, such as muscular and neuromuscular pathologies, e.g., a muscle dystrophy, a myopathy, a disease of peripheral nerves, a metabolic muscle disorder, a vasospasm, a heart arrhythmia, and/or a cardiomyopathy, suitable cells include cardiac muscle cells, ventricular cardiac muscle cells, atrial cardiac muscle cells, striated muscle cells, smooth muscle cells, vascular smooth muscle cells, and combinations thereof. In the case of a disorder of pancreatic islet cells, e.g., impaired glucose tolerance, diabetes, insulinoma, suitable cells include pancreatic islet cells as described herein; in the case of a disorder of adipocytes, e.g., lipodystrophy, liposarcoma, suitable cells include adipocytes as described herein; in the case of a myoepithelial disorder, e.g., myoepithelial carcinoma, suitable cells include salivary gland cells, myoepithelial cells and combinations thereof; in the case of a luminal disorder, e.g., a vascular disorder, suitable cells include vascular smooth muscle cells. In one embodiment, spheroids and, more particularly, tumor spheroid cells can be used, although it should be understood that any other cell types can be used.

Although it should be understood that any cell type can be used in the devices and methods of the invention, non-limiting examples of suitable cells or cell clusters for use in the present invention include, for example, cardiac muscle cells, ventricular cardiac muscle cells, atrial cardiac muscle cells, striated muscle cells, smooth muscle cells, vascular smooth muscle cells, pancreatic islet cells, adipocytes, salivary gland cells, myoepithelial cells spheroids, and tumor spheroid cells, and combinations thereof.

Suitable cells for use in the invention can be normal cells, abnormal cells (e.g., those derived from a diseased tissue, or those that are physically or genetically altered to achieve an abnormal or pathological phenotype or function), normal or diseased pancreatic islet cells, normal or diseases adipocytes, stem cells (e.g., embryonic stem cells), or induced pluripotent stem cells.

In some embodiments, cells clusters are encapsulated in a hydrogel.

As used herein, the term "pancreatic islet cell" includes pancreatic islet cells derived from an adult organism or an embryonic organism, pancreatic islet cell precursor cell types or stem cells that will develop into pancreatic islet cells. Similarly, the term "adipocyte" includes adipocytes e.g., white, brown, or "beige"/"brite" adipocytes derived from an adult organism or an embryonic organism, adipocyte precursor cell types or stem cells that will develop into adipocytes.

Exemplary cells that can be used include stem cells, pancreatic acinar cells, islets of Langerhans, adipocytes, preadipocytes, biliary epithelial cells, and the like. In some embodiments, the cells can be adult stem cells, such as, in some embodiments, adipose-derived stem cells, pancreatic stem cells, and the like. In some particular embodiments, the adult stem cells can be adipose-derived stem cells which may differentiate to pancreatic progenitor cells.

In one embodiment, the cells can be pancreatic beta-cells. Suitable pancreatic beta-cells can be, for example, from species such as mouse, rat, human, guinea pig, hamster, pig, dog, sheep, goat, donkey or cow, and are used either in the form of islets of Langerhans or isolated cells. The cell line can be, for example, selected from the rat insulinoma (RIN) cell lines such as INS-1 (see, e.g., Asfari et al. *Endocrinol.*, 130, 167 (1992)), INS-2 (see, e.g., Asfari et al., *Endocrinol.*, 130, 167 (1992)), RIN-r (see, e.g., Philippe et al., *Endocrinol.* 119, 2833 (1986)), and RIN-m (see, e.g., Bathena et al., *Diabetes* 31, 521 (1982); Praz et al., *Biochem. J.* 210, 345 (1983); Philippe et al. *J. Clin. Invest.* 79, 351(1987)) or from the hamster insulinoma (HIT) cell lines such as HIT-T15 (see, e.g., Santerre et al., *Proc. Natl. Acad. Sci. U.S.A.* 78, 4339 (1981)) or from mouse beta-cell lines expressing the SV40 large T-antigen (beta-TC lines) such as betaTC1, betaTC2, betaTC3 (see, e.g., Efrat et al., *Proc. Natl. Acad. Sci. U.S.A.* 85, 9037(1988)), betaTC6 (see, e.g., Poitout et al., *Diabetes* 44, 306 (1995)), betaTC7 (see, e.g., Efrat et al., *Diabetes* 42, 901(1993)), betaTCtet (see, e.g., Efrat et al., *Proc. Natl. Acad. Sci. U.S.A.* 92, 3576 (1995)) or from mouse insulinoma (MIN) cell lines such as MIN6 (see, e.g., Myazaki et al., *Endocrinol.* 127, 126(1990)).

Suitable adipocytes include, isolated adipose tissue (such as brown adipose tissue or white adipose tissue), isolated cells (such as primary adipocytes or adipocyte cell lines), or a combination thereof. In some embodiments, an adipose cell-line can be employed. Exemplary cells include, but are not limited to, 3T3-L1 cells, PAZ6 cells, T37i cells, 3T3-F442A cells, and/or HIB-1B cells. Any of a variety of isolated cells (such as cell lines) can be used.

The aforementioned cells/cell-lines can be optionally transformed to express a variety of growth factors and/or agents. The reagents and markers useful for such purposes are known in the art (see, e.g., U.S. Pat. No. 8,389,207, the contents of which are incorporated by reference herein).

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a an object including pancreatic islet cells or adipocytes with a test compound) is intended to include any form of interaction (e.g., direct or indirect interaction) of a test compound and the cells.

Test compounds can be any agents including chemical agents (such as toxins), small molecules, pharmaceuticals, peptides, proteins (such as antibodies, cytokines, enzymes, and the like), nanoparticles, and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. (See, e.g., *Molecular Cloning A Laboratory Manual* (1989), 2nd Ed., ed. by Sambrook, Fritsch and Maniatis, eds., Cold Spring Harbor Laboratory Press, Chapters 16 and 17; U.S. Pat. No. 4,683,195; *DNA Cloning, Volumes I and II*, Glover, ed., 1985; Oligonucleotide Synthesis, M. J. Gait, ed., 1984; *Nucleic Acid Hybridization*, D. Hames & S. J. Higgins, eds., 1984; *Transcription and Translation*, B. D. Hames & S. J. Higgins, eds., 1984; *Culture Of Animal Cells*, R. I. Freshney, Alan R. Liss, Inc., 1987; *Immobilized Cells And Enzymes*, IRL Press, 1986; Perbal (1984), *A Practical Guide To Molecular Cloning*; See Methods In Enzymology (Academic Press, Inc., N.Y.); *Gene Transfer Vectors For Mammalian Cells*, J. H. Miller and M. P. Calos, eds., Cold Spring Harbor Laboratory, 1987; *Methods In Enzymology*, Vols. 154 and 155, Wu et al., eds., Academic Press Inc., N.Y.; *Immunochemical Methods In Cell And Molecular Biology* (Mayer and Walker, eds., Academic Press, London, 1987; *Handbook Of Experimental Immunology*, Volumes I-IV, D. M. Weir and C. C. Blackwell, eds., 1986).

Portions of the present invention are illustrated by the following examples which should not be construed as limiting. The entire contents of all references, patents and published patent applications cited throughout this application, as well as the Figures, are hereby incorporated herein by reference.

While the device design was inspired by human pancreatic islets, which each receive parallel perfusion from one to three designated capillaries per islet, the device may be used for organoids or cell clusters from any tissue, e.g., adipose. In a similar vein, it should be noted that the chip can be designed to accommodate clusters of many sizes. In doing so, the height and width of every channel should be larger than that of the largest cluster. Additionally, the trap dimensions should be large enough to accommodate a single cluster, but not large enough to risk the trapping of more than one. Clusters encapsulated within a hydrogel may also be trapped in this fashion.

In some embodiments, a microfluidic chip will also accommodate plugging of a reservoir, using a plug designed specifically for the chip into the inlets of the chip. The volume and height of the reservoir will be calibrated so that when a suspension of clusters is introduced to the reservoir when it is attached to the chip, gravity will cause the clusters to flow into the chip and be trapped within a certain period of time. During the trapping, while the suspension flows through the chip, it can be placed in an incubator to ensure that cells remain at their desired temperature. If traps are not filled from the first introduction of the cell cluster suspension, the same suspension that came out of the outlet of the chip can then be used to populate the empty traps until all are filled.

In some embodiments, objects can be released and recovered from the chip by applying a pressure at one or more outlets that reverses a direction of flow causing the objects to flow out an inlet of the chip.

Aside from long term culture, the device may be modified to allow for analysis of cell function either at discrete time points or even in real time. For instance, protein secretions of the cells may be siphoned off downstream of the cartridge and quantified through techniques such as ELISA or more a sophisticated continuous on-line protein sensor. Due to the optical clarity of the chip from thermal bonding on a glass surface, the cell clusters may be imaged while isolated within the chip, and may possibly be fixed for immunostaining in situ as well. It should be noted that since the clusters are captured in specific locations due to the traps, a single control program on a microscope may be used for reproducibly imaging the cells on every chip. By applying pressure at the outlet, the trapped cell clusters may also be dislodged and captured from the inlets. Retrieval of the clusters in this fashion may allow for running genetic, expression, and proteomic data, or for histology.

V. Examples

Example 1: Influence of Serial Flow Versus Parallel Flow on Oxygen Concentrations To determine the influence of serial flow versus parallel flow on a conditions for islets arranged in series, a 3D finite element model of flow, oxygen convention-diffusion and oxygen consumption was conducted and demonstrated how a serial arrangement of islets in a flow path significantly affected the environment experienced by downstream islets as shown in FIG. 9. The model was based on work by Buchwald (Buchwald, P. Theor Biol Med Model, 2011). The model assumed incompressible flow and 5 islets each having a diameter of 250 μm encapsulated in 125 μm micron thick hydrogel. The channel initial conditions were 0.21 mM oxygen and the gel and islet initial conditions were 0 mM oxygen. The flow rate was 4 μL/M.

Example 2: Evolution of Trap Design

To achieve trapping of the spheres, a large number of trap designs were evaluated using both simulations and physical prototypes. A trap consists of a constriction in a channel smaller than the object to be trapped (for islets, this was 75-100 μm, although this could conceivably range from 10

μm to 1 mm) and a side channel (also referred to herein as a bypass channel) that circumvents the trapping region, with dimensions large enough for passage of the object of interest. A successful trap has lower flow resistance than in the accompanying side channel, ensuring that an object of interest that approaches will be directed towards the trap. However, an additional criterion for success is to trap only a single object. To accomplish this, the resistance of the side channel must be less than that of the trap once a trap has been filled by one object. In this case, any objects that approach a trap after it has been filled will flow around the trap through the side channel.

Dozens of trap motifs were designed and modeled with finite element simulations to determine the ratio of flow rate (see FIG. 11). Theoretically, the trap with the best chance of capturing a cluster is one where the flow rate through the side channel ($Q_{side}$) is as low as possible relative to that of the flow rate through the constriction ($Q_{trap}$), such that the ratio between the two ($Q_{side}/Q_{trap}$) approaches or is less than 1. Traps were designed to make particular comparisons between parameters such as the size, geometry and constriction type.

A number of trap designs were created and evaluated with these conditions in mind, with the added concern being the ability to fabricate such traps in a polymeric plastic such as polycarbonate. One of the main fabrication tools available for manufacturing prototypes with such plastics is CNC milling, which is limited by the size of the end mills (typically 1/64"). Each trap motif in a channel was drawn with a CAD program, converted to an .STL mesh, and imported into COMSOL. Occasionally, mesh import settings needed to be adjusted to allow for proper feature recognition. For each trap, a three-dimensional Navier-Stokes model of flow was generated to simulate flow through the trap in the anticipated operation range of the device. After the simulation had been solved, the flow velocity was integrated across the cross sectional sections of both the trap region and the side channel region to get the flow rate through each, in some cases multiple times per trap to account for different locations along the main axis of the channel.

As they were generated, traps designs evolved to consider parameters such as trap size, geometry and constriction type. Traps that could be made with a CNC mill could have either a constriction in the height of the channel (where the entire body of the trap was milled out of the bottom layer of the device in the floor of the channel) or a constriction in the width of the channel. A solution to creating a small (~75 μm) width constriction was to compose the final trap of two halves, one of which would be milled on the top layer of the chip (on the ceiling of the channel) and the other milled on the bottom/channel layer of the device (coming up from the floor). Alignment posts outside of the channel enabled proper positioning of the two trap halves when assembling the two pieces together. In later trap versions, the use of both width and height constrictions opened up the cross section of the trap to allow more flow through the trap. Variations in the size of the constriction, the size and shape of the side channel, and the overall trap geometry were all modeled as well. Traps with a semicircular profile were eventually adopted to reduce the total volume of the constriction, ensuring that the smallest cross sectional area only occurred at a single point and thus allowed for more flow through the entire trap as a whole. In the initial stages of design, as many as two dozen trap designs were evaluated in this manner. FIG. 10 includes perspective an planar views of trap designs evaluated.

Traps with the highest estimated flow through the trapping region were fabricated into a prototype polycarbonate chip and tested using either density-matched microbeads (density of 1.08 kg/m³) and then clusters of stem-cell derived R cells, both with diameters around 250 μm diameter. After the first round of testing, the trap designs that performed the best were further refined by increasing the length of the side channel to increase the resistance in the traps. Approximately eight new designs were modeled as described before, and the trap motif with the highest flow through the trap was chosen for experimental validation. The second test with a prototype demonstrated robust capture of cell spheres in multiple copies of this cell trap motif. FIG. 11 depicts the method for calculating the flow rate and an overview of parameter varied to asses trap efficacy including a process for determining a ratio of flow through a side branch versus flow through the trap ($Q_{side}/Q_{trap}$), which included finite element flow simulation and integration of the velocity profile for the trap. A low value for the ratio is desirable for an unfilled trap to obtain preferential flow into the unfilled trap.

FIG. 12 includes image of CAD drawings for various trap designs (left) and a prototype chip (right) that was manufactured and tested using the trap designs that performed best in simulations. Trap designs E and H performed best at trapping microspheres and cells clusters in preliminary experiments. However, because multiple cell clusters were captured in individual traps during the second test, the next design goal was to adjust the side channel length to balance the preference for spheres to enter the trap and the side channel. A CAD drawing of the trap without the side channel was created to estimate the flow resistance in the trap with a simulated cell cluster. A combined Navier-Stokes and Brinkman flow simulation with this trap filled by a porous sphere of 200 or 250 μm in diameter (porosity of 0.1 and permeability of 1E-15 m²) was then used to simulate a captured object. The pressure drop across the trap was computed in each case, and the case with the highest drop used to compute the hydrodynamic resistance. By estimating how the hydrodynamic resistance in the side channel varied as a function of its length, it was possible to find a side channel length where the resistance in the side channel equaled that of a blocked trap.

A microfluidic chip including traps these lengthened side channels was fabricated and is described below with respect to Example 3. These traps were incorporated into a device with a combined downstream continuous sensor for quantifying the amount of analyte in real time. After experiments and time-dependent, convection/diffusion modeling of analyte traveling from one end of the combined chip to the other, it was determined that the side channels in the trap were sequestering flow and causing disruptions in the propagation of the signal from one end of the chip to another. To account for this issue, the traps were redesigned.

In the redesign, traps were arranged in a bifurcating design, where the path length and channel volume leading to each individual trap was identical. This ensured that a stimulus signal was delivered in parallel to each trap without distortions. Instead of a single side channel for each trap, the side channel was placed prior to the first bifurcation leading to the traps. Similar to the process for a single trap described above, the length of the single side channel was determined by modeling flow through a device with multiple traps filled with captured objects. The side channel length was made such that the resistance matched that of the device with all but one trap filled. Microfluidic chips including traps these lengthened side channels was fabricated and are described below with respect to Example 4. Devices that aim to test the input/output dynamics of captured objects of interest should use this single side channel design. However, the trapping motif where each trap has its own side channel is certainly a viable trapping strategy for other applications.

Additional modeling has been done to investigate shear forces of flow on a trapped object, oxygen delivery to a trapped object, and parallel delivery of time-dependent stimuli.

The evolution of the trap design and chip design involved more than 200 hours of modeling, fabrication, and experiments.

Example 3: Microfluidic Chip Including Trapping Channels Each Having a Bypass Channel A microfluidic chips were manufactured and tested where each trapping channel had an associated bypass channel similar to the embodiment shown in FIG. 4. Each trap included a lateral gap width of 75 µm, and a trapping channel height of 40 µm. The body was made from milled polycarbonate. The specifications of the chip are listed below:
Body Material: Polycarbonate
Internal volume: 128.18 µL
Hydrodynamic Resistance: 2.14 Pa*min/mm$^3$
Pressure drop at 1 µL/min: 2.08 Pa
Number of islets/traps: 10
Estimated shear on islets in culture: <1.1 mPa (target: <6 mPa)
Oxygenation: 14.2 pmol/min*islet (target: 3.6 pmol/min*islet)

After priming of the microchip, complete cell cluster loading took no more than 30 seconds. FIG. 13 includes images of an islet cell clusters trapped in two different traps.

As noted above, this trap design was determined to sequester flow and caused disruptions in the propagation of an input signal from one end of the chip to another. Results of a simulation for propagation of a change in an input signal that show this sequestration of flow are shown in FIG. 14. The side channels appear to store the signal and dampen the signal in the trapping channels.

Example 4: Microfluidic Chip Including Trapping Channels and One Bypass Channel

As noted above, a redesign of the chip involved using a single bypass channel upstream of the plurality of trapping channels, where the single bypass channel has a separate outlet from that of the plurality of trapping channels. This allowed the bypass channel to be blocked after loading of objects or clusters. The microfluidic chip whose design is shown in FIGS. 1A-2C was fabricated from polycarbonate using CNC milling. Each trap had a lateral gap of 75 µm, a trapping channel width of 400 µm, and a trapping channel height of 400 µm. FIG. 15 includes images of the trapping portion of the chip and an islet trapped in a trap of the chip. The trap design was also simulated to verify that the blocked bypass channel did not cause disruptions in the propagation of an input signal from one end of the chip to another. Results of the simulation are shown in FIG. 17. The results demonstrated that temporal changes in the input were translated accurately to temporal changes in flow at the traps. These results were also experimentally verified using the chip.

Example 5: Microfluidic Chip Including Hydrophobic Membranes

During long term culture, formation of gas bubbles was observed in the microfluidic channels. A modified microfluidic chip was produced that incorporated multiple hydrophobic membranes between the first portion and the second portion of the device, with holes through the second portion to the hydrophobic membranes to provide for gas exchange. The hydrophobic membranes had a water entry pressure higher than the operating pressure of the chip (about 14.5 psi) to enable gas exchange with various channel without leaking of liquid through the membranes. The material of the membranes was PTFE and polypropylene with a pore size of 0.1 to 0.2 µm and a water entry pressure of greater than 60 psi. FIG. 17 includes an image of gas bubbles in trapping channels and an images of membranes disposed over multiple portions of the chip. The membranes did not interfere with bonding of the top portion and bottom portion of the chip during manufacturing and did not cause leakage.

Example 6: Simulations for Mixing Channel

The inventors also performed simulations to determine dimensions of a mixing channel required to efficiently mix a stimulant, specifically glucose, between two different input channels prior to delivering the fluid to the trapping channels. The model is depicted in FIG. 18 and the results of the modeling and simulation are shown in FIG. 19. Diluted species are transported through convection (e.g., fluid flow) and diffusion (e.g., particle motion). In a microfluidic device, mixing occurs primarily through diffusion due to laminar flow as illustrated in the schematic drawing on the left of FIG. 18. The diffusivity is a property of a molecule in a flowing solution.

A scaling law approximation of mixing length was applied. The model was constructed for diffusion of glucose in solution. The model assumed that mixing occurs when the glucose has traversed the channel width, that there is incompressible flow, that the glucose diffusivity in solution is 4.0E-10 m$^2$/s, and that the outlet is at atmospheric pressure. The results indicated that a mixing length of about 9 mm was need for a 0.4 mm by 0.4 mm channel.

Example 7. Methods and Material

Materials Used
All polycarbonate sheets were purchased from McMaster Carr. Dichloromethane was obtained from Sigma Aldrich. Isopropanol was obtained through VWR.
Chip Design
Design of the chip was conducted on Solidworks Premium 2017 (Dassault Systemes SolidWorks Corporation) through a licensed copy of the program purchased by the Wyss Institute. Finite element modeling was done using COMSOL (COMSOL, Inc.) with a licensed copy of the program provided by Harvard SEAS.
Chip Fabrication
The two chip layers were cut on a Roland ModelaProII CNC mill out of polycarbonate stock material. After sanding down the faces of the chip on a flat surface (using 400 and 600 grit sand paper), the layers were cleaned by submerging in 100% isopropanol and sonicating for 20 minutes. The layers were removed and dried using an air gun. Following cleaning, pieces were polished on all sides with a quick treatment of heated dichloromethane vapor (at 325° C.) and left to sit in a chemical hood for at least 6 hours. The two chip layers were then placed together using the alignment posts and sandwiched between two layers of borosilicate glass of at least ⅛" thick cut to the same dimensions as those of the chip (using a water jet). The sandwiched chip was then placed between rubber mats and steel shims (one on each side) and placed within a heated hydraulic press. The layers were preheated to 139° C. and then bonded under a pressure of around 0.33 MPa for 30 minutes at this temperature. While pressure is maintained, the chip was then allowed to cool to room temperature over the course of the next 4-5 hours.

EQUIVALENTS

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties are specified herein for embodiments of the invention, those parameters can be adjusted up or down by 1/20th, 1/10th, 1/5th, 1/3rd, 1/2, etc., or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. The contents of all references, including patents and patent applications, cited throughout this application are hereby incorporated by reference in their entirety. The appropriate components and methods of those references may be selected for the invention and embodiments thereof. Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A microfluidic chip for trapping a plurality of objects, the microfluidic chip comprising:
    a body including:
        one or more upstream inlets;
        one or more downstream outlets;
        a first plurality of trapping channels having a collective flow resistance and comprising three or more parallel trapping channels, wherein each trapping channel of the first plurality of trapping channels is fluidically connected to the one or more upstream inlets and to the one or more downstream outlets and has a trapping channel length and comprises one single hydrodynamic trap and no other hydrodynamic traps, the single hydrodynamic trap defined by a structural constriction in a respective trapping channel configured to:
            trap an object having a diameter in a range of 10 microns to 1 mm, and
            direct all of a fluid flowing into the respective trapping channel into the single hydrodynamic trap of the respective trapping channel,
        wherein for each trapping channel in the first plurality of trapping channels, the one or more upstream inlets and the respective trapping channel up to the single hydrodynamic trap defines:
            a flow path distance from the one or more inlets to the respective single hydrodynamic trap wherein the flow path distance of each trapping channel of the first plurality of trapping channels is identical across the first plurality of trapping channels, and
            a channel volume from the one or more upstream inlets to the respective single hydrodynamic trap, wherein the channel volume of each trapping channel of the first plurality of trapping channels is identical across the first plurality of trapping channels;
        a main channel upstream of the first plurality of trapping channels, the main channel fluidically connected to the first plurality of trapping channels; and
        a bypass channel having a bypass channel length, a bypass channel flow resistance, a bypass channel upstream end, and a bypass channel downstream end, the bypass channel parallel to the first plurality of trapping channels,
        wherein the bypass channel branches from the main channel upstream of the fluidic connection to the first plurality of trapping channels, bypasses the first plurality of trapping channels, and does not include any hydrodynamic traps;
        wherein the bypass channel upstream end is fluidically connected to the one or more upstream inlets and the bypass channel downstream end is fluidically connected to the one or more downstream outlets;
        wherein the bypass channel length is longer than each trapping channel length and the bypass channel flow resistance is higher than the first plurality of trapping channels collective flow resistance when two or more single hydrodynamic traps of the first plurality of trapping channels contain no trapped object; and
        wherein the bypass channel flow resistance is lower than the first plurality of trapping channels collective flow resistance when the single hydrodynamic trap of each respective trapping channel in the first plurality of trapping channels includes a trapped object.

2. The microfluidic chip of claim 1 wherein the one or more downstream outlets includes:
    a bypass output configured to receive a first output from the bypass channel, and
    one or more trap outputs configured to receive a second output from the first plurality of trapping channels and not receive the first output from the bypass channel.

3. The microfluidic chip of claim 1 wherein the bypass output is configured to reduce or stop a flow into the bypass channel by being partially blocked or by being blocked, respectively, after a completion of a loading of the microfluidic chip with objects.

4. The microfluidic chip of claim 1 wherein the one or more upstream inlets, the first plurality of trapping channels, and the one or more downstream outlets define a plurality of flow paths, each flow path of the plurality of flow paths defined from the one or more upstream inlets through a respective single trapping channel and to the one or more downstream outlets, each flow path in the plurality of flow paths having a same flow path resistance when no hydrodynamic trap in the first plurality of trapping channels has a trapped object.

5. The microfluidic chip of claim 1 wherein each trapping channel of the first plurality of trapping channels has a trapping channel width and a trapping channel height, and wherein, for each trapping channel of the first plurality of trapping channels, at the respective single hydrodynamic trap, the trapping channel width narrows over at least a portion of the trapping channel height.

6. The microfluidic chip of claim 1 wherein the first plurality of trapping channels include an upstream side and the one or more upstream inlets comprises two or more upstream inlets, and wherein the microfluidic chip includes a mixing channel fluidically connected to the two or more upstream inlets and to the upstream side of the first plurality of trapping channels.

7. The microfluidic chip of claim 1 wherein each trapping channel of the first plurality of trapping channels includes:
   a base surface;
   a top surface opposite the base surface;
   a first sidewall; and
   a second sidewall opposite the first sidewall, each trapping channel having a first hydrodynamic trap height at a respective single hydrodynamic trap;
   wherein the respective single hydrodynamic trap of each trapping channel includes:
      a first protrusion extending from the first sidewall toward the second sidewall and extending from the base surface toward the top surface of the trapping channel, with the first protrusion having a first protrusion height less than the first hydrodynamic trap height forming a first shelf with a first top gap separating the first shelf from the top surface of the trapping channel; and
      a second protrusion extending from the second sidewall toward the first sidewall and extending from the top surface toward the base surface of the trapping channel, with the second protrusion having a second protrusion height less than the first hydrodynamic trap height forming a first overhang with a first bottom gap separating first overhang from the base surface of the trapping channel, the second protrusion disposed opposite the first protrusion such that a first lateral gap separates the first protrusion and the second protrusion over a portion of the first hydrodynamic trap height.

8. The microfluidic chip of claim 7 wherein, for each of the plurality of trapping channels, the single hydrodynamic trap of the respective trapping channel includes a narrowing of the respective trapping channel at the first lateral gap configured to trap an object, and wherein the first top gap and the first bottom gap enable a fluid to flow around an object trapped in the first lateral gap.

9. The microfluidic chip of claim 7 wherein the body includes:
   a first portion having a first surface; and
   a second portion having a second surface, the second portion attached to, coupled to, or fused with the first portion;
   wherein for each trapping channel in the first plurality of trapping channels, the first sidewall and the first protrusion of the single hydrodynamic trap of the respective trapping channel are formed by one or more recesses in the first surface of first portion facing the second portion; and wherein the second sidewall and the second protrusion of the single hydrodynamic trap are formed by one or more projections from the second surface of the second portion facing the first surface of the first portion.

10. The microfluidic chip of claim 1 wherein the body includes:
    a first portion including a first surface having one or more recesses; and
    a second portion including a second surface having one or more projections, the second portion attached to, coupled to, or fused with the first portion, wherein the one or more recesses of the first portion and the one or more projections of the second portion define the single hydrodynamic traps of the first plurality of trapping channels, wherein each single hydrodynamic trap includes:
       a first protrusion of a first sidewall of a respective trapping channel wherein the first sidewall and the first protrusion are formed by the one or more recesses of the first portion; and
       a second protrusion of a second sidewall opposite the first protrusion formed by the one or more projections of the first portion, the first protrusion and the second protrusion separated by a lateral gap over at least a portion of a height of a respective trapping channel at the single hydrodynamic trap.

11. The microfluidic chip of claim 1 further comprising:
    a second plurality of trapping channels, each trapping channel of the second plurality of trapping channels parallel to each other and disposed downstream of the first plurality of trapping channels, each trapping channel of the second plurality of trapping channels including a second single hydrodynamic trap configured to trap an object having a diameter smaller than 10 microns.

12. A method of making the microfluidic chip of claim 9, the method comprising:
    forming the first portion with the first surface having the one or more recesses;
    forming the second portion with the second surface having the one or more projections; and
    attaching, coupling or fusing at least a portion of the first surface of the first portion to at least a portion of the second surface of the second portion, wherein the one or more recesses of the first portion and the one or more projections of the second portion define the single hydrodynamic traps of the first plurality of trapping channels.

13. A method of loading and culturing cells, the method comprising:
    providing the microfluidic chip of claim 1;
    hydrodynamically trapping an object comprising one or more cells in each hydrodynamic trap by delivering a fluid including a plurality of objects into the one or more upstream inlets, each object of the plurality of objects comprising the one or more cells; and
    culturing the one or more cells of each object in each single hydrodynamic trap by delivering a cell culture medium to the microfluidic chip.

14. A method of identifying a test compound for modulating cell differentiation, cell viability, cell function, or a combination thereof, the method comprising:
    providing the microfluidic chip of claim 1;
    hydrodynamically trapping an object comprising one or more cells in each hydrodynamic trap by delivering a fluid into the one or more upstream inlets, the fluid including a plurality of objects, each object of the plurality of objects comprising the one or more cells;
    contacting the trapped objects with a test compound; and
    identifying the test compound for modulating cell differentiation, cell viability, or function or a combination thereof by determining a presence effect and an absence effect of the test compound on cell differentiation, cell viability, cell function, or a combination thereof in a presence of the test compound and in an absence of the test compound, wherein a modulation of cell differentiation, cell viability, cell function, or a combination thereof in the presence of said test compound as compared to cell differentiation, cell viability, cell function, or a combination thereof in the absence of said test compound indicates said test compound modulates cell differentiation, cell viability, cell function, or a combination thereof.

15. A method of identifying a compound useful for treating a disease or a disorder, the method comprising:
providing the microfluidic chip of claim 1;
hydrodynamically trapping an object comprising one or more cells in each single hydrodynamic trap by delivering a fluid into the one or more upstream inlets, the fluid including a plurality of objects, each object of the plurality of objects comprising the one or more cells;
contacting the trapped objects with a test compound; and
identifying a compound useful for treating the disease or the disorder by determining a presence effect and an absence effect of the test compound on cell differentiation, cell viability, cell function, or a combination thereof in a presence of the test compound and in an absence of the test compound, wherein a modulation of cell differentiation, cell viability, cell function, or a combination thereof in the presence of said test compound as compared to cell differentiation, cell viability, cell function, or a combination thereof in the absence of said test compound indicates said test compound modulates cell differentiation, cell viability, function, or a combination thereof.

* * * * *